(12) United States Patent
Karchin et al.

(10) Patent No.: US 11,786,142 B2
(45) Date of Patent: Oct. 17, 2023

(54) INGESTIBLE RFID TAG AND READER SYSTEM

(71) Applicant: TOKITAE LLC, Bellevue, WA (US)

(72) Inventors: Ari Karchin, Seattle, WA (US); Mark S. Freeman, Redmond, WA (US); Fridrik Larusson, Seattle, WA (US); Steven A. Rodriguez, Seattle, WA (US); Lowell L. Wood, Jr., Bellevue, WA (US)

(73) Assignee: TOKITAE LLC, Bellevue, WA (US)

( * ) Notice: Subject to any disclaimer, the term of this patent is extended or adjusted under 35 U.S.C. 154(b) by 918 days.

(21) Appl. No.: 16/737,126

(22) Filed: Jan. 8, 2020

(65) Prior Publication Data

US 2020/0221972 A1 Jul. 16, 2020

Related U.S. Application Data

(60) Provisional application No. 62/791,085, filed on Jan. 11, 2019.

(51) Int. Cl.
*A61B 5/07* (2006.01)
*A61B 5/00* (2006.01)
(Continued)

(52) U.S. Cl.
CPC .............. *A61B 5/073* (2013.01); *A61B 5/062* (2013.01); *A61B 5/6861* (2013.01); *A61B 90/98* (2016.02);
(Continued)

(58) Field of Classification Search
CPC ....... A61B 5/073; A61B 5/062; A61B 5/6861; A61B 90/98; A61B 5/14539;
(Continued)

(56) References Cited

U.S. PATENT DOCUMENTS

2002/0055734 A1* 5/2002 Houzego ............. A61M 31/002
604/891.1
2005/0147559 A1 7/2005 Alten
(Continued)

FOREIGN PATENT DOCUMENTS

KR 1020140051299 A 4/2014

OTHER PUBLICATIONS

PCT International Search Report; International Appl. No. PCT/US2020/012847; dated Jun. 9, 2020; pp. 1-7.
(Continued)

*Primary Examiner* — Omeed Alizada
(74) *Attorney, Agent, or Firm* — AEON Law, PLLC; Adam L. K. Philipp; Shan Liao

(57) ABSTRACT

Ingestible radio frequency identification (RFID) tags are disclosed. A system embodiment includes, but is not limited to, an RFID tag including a flexible substrate foldable between a planar configuration and a tubular configuration, a conductive element disposed on the flexible substrate, and an RFID tag chip electrically coupled with the conductive element; a capsule structured and dimensioned for ingestion by a biological subject, the capsule including a shell structured and dimensioned to enclose a medication for the biological subject simultaneously with the RFID tag when the flexible substrate is in the tubular configuration, but not when the flexible substrate is in the planar configuration; and a pH switch structure coupled to an exterior surface of the capsule, the pH switch configured to deactivate the RFID tag in a first configuration and to permit activation of the RFID tag in a second configuration within the biological subject.

25 Claims, 29 Drawing Sheets

(51) Int. Cl.
*A61B 5/06* (2006.01)
*A61B 90/98* (2016.01)
*G06K 19/077* (2006.01)
*H01Q 1/22* (2006.01)
*A61J 1/03* (2023.01)
*A61B 5/145* (2006.01)

(52) U.S. Cl.
CPC ............ *A61J 1/03* (2013.01); *G06K 19/0779* (2013.01); *G06K 19/07783* (2013.01); *H01Q 1/2216* (2013.01); *A61B 5/14539* (2013.01); *A61B 2562/162* (2013.01); *A61J 2200/30* (2013.01); *A61J 2205/60* (2013.01)

(58) Field of Classification Search
CPC ... A61B 2562/162; A61J 1/03; A61J 2200/30; A61J 2205/60; G06K 19/07783; G06K 19/0779; G06K 7/10009; G06K 17/00; G06K 19/041; G06K 19/0723; G06K 19/07771; G06K 19/07773; H01Q 1/2216; H01Q 1/2225; H01Q 1/273; H01Q 7/00; G16H 20/13
See application file for complete search history.

(56) References Cited

U.S. PATENT DOCUMENTS

| | | | |
|---|---|---|---|
| 2006/0289640 A1* | 12/2006 | Mercure | A61J 3/007 340/572.1 |
| 2007/0238942 A1* | 10/2007 | Baylor | G01N 33/84 600/309 |
| 2013/0002423 A1 | 1/2013 | Robertson et al. | |
| 2013/0245663 A1 | 9/2013 | Voss et al. | |
| 2018/0132784 A1* | 5/2018 | Euliano | A61B 5/42 |

OTHER PUBLICATIONS

Extended European Search Report and Search Opinion received for EP Patent Application No. 20738532.9, dated Sep. 5, 2022, 8 pages.

* cited by examiner

FIG. 14

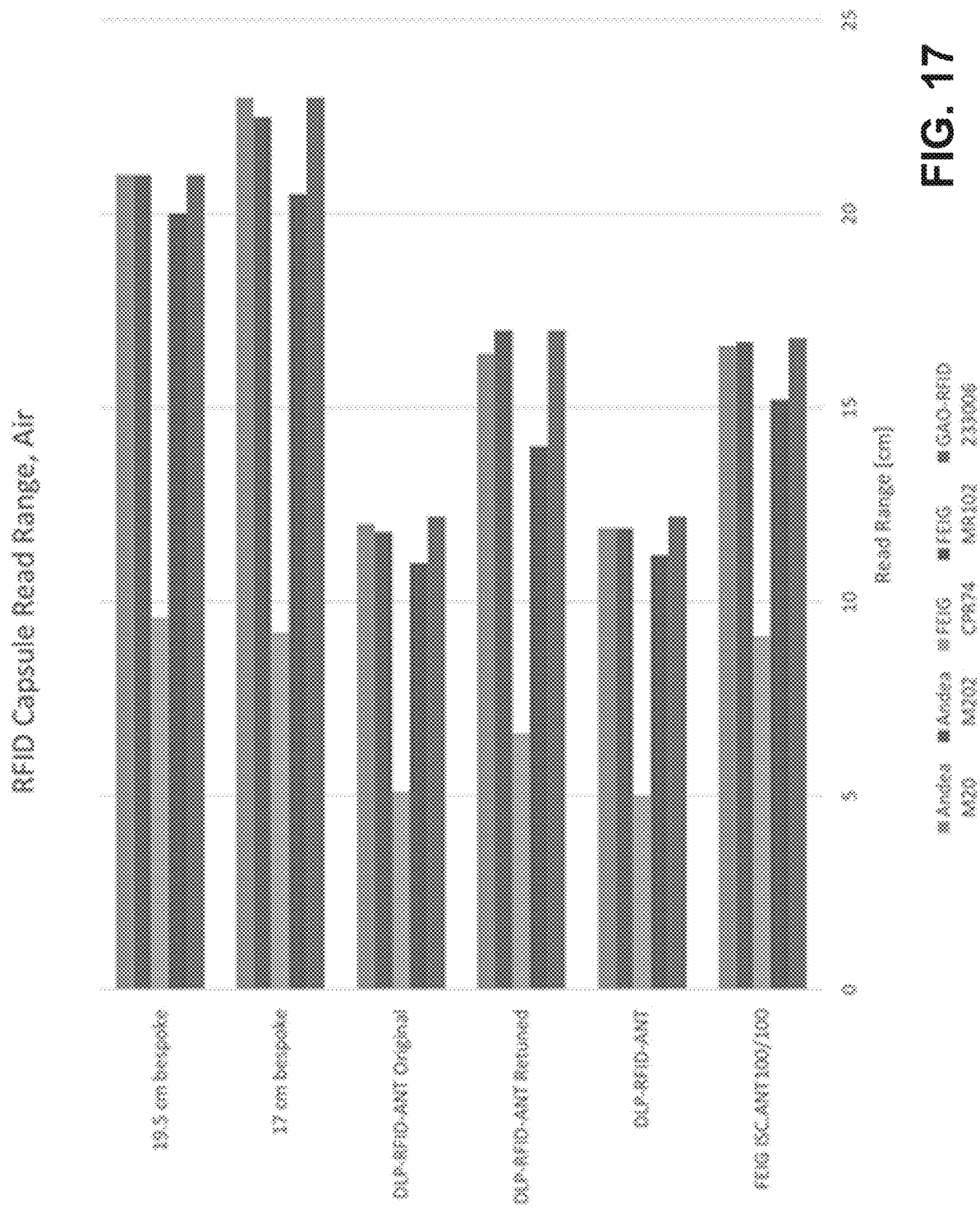

| SN | Notes | Capsule | Capacitor [pF] | Resonant Frequency [MHz] | Industrial Reader, 9 cm coil Read Range [cm] | |
|---|---|---|---|---|---|---|
| | | | | | Air | Saline |
| C2 | CLR-THIXO epoxy coated | 00 | 43 | 13.35 | 15.4 | 15.2 |
| C3 | CLR-THIXO epoxy coated | 00 | 39 | 13.86 | 14 | 14.3 |
| C4 | CLR-THIXO epoxy coated | 00 | 41 | 13.64 | 15.8 | 16 |
| C5 | CLR-THIXO epoxy coated | 000 | 43+2.8 | 13.75 | 16.8 | 17.1 |
| C6 | CLR-THIXO epoxy coated | 000 | 43+2.8 | 13.7 | 17 | 17.2 |
| C7 | CLR-THIXO epoxy coated | 000 | 43.3.3 | 13.66 | 17 | 16.5 |
| C8 | CLR-THIXO epoxy coated | 000 | 43 | 13.98 | 15.8 | 16.6 |
| D1 | CLR-THIXO epoxy coated | 000 | 43 + 3 | 13.73 | 17.2 | 17.5 |
| D2 | CLR-THIXO epoxy coated | 000 | 47 | 13.57 | 18 | 15.4 |
| D3 | CLR-THIXO epoxy coated | 00 | 43 | 13.60 | 16 | 15.5 |
| D4 | CLR-THIXO epoxy coated | 00 | 39 + 3 | 13.68 | 16.5 | 16.5 |
| D5 | CLR-THIXO epoxy coated | 00 | 39 + 3.3 | 13.7 | 15.6 | 15.7 |
| D6 | CLR-THIXO epoxy coated | 00 | 43 + 1.3 | 13.48 | 16 | 16 |
| D7 | CLR-THIXO epoxy coated | 000 | 43 + 3.6 | 13.82 | 15.9 | 17.2 |

FIG. 18

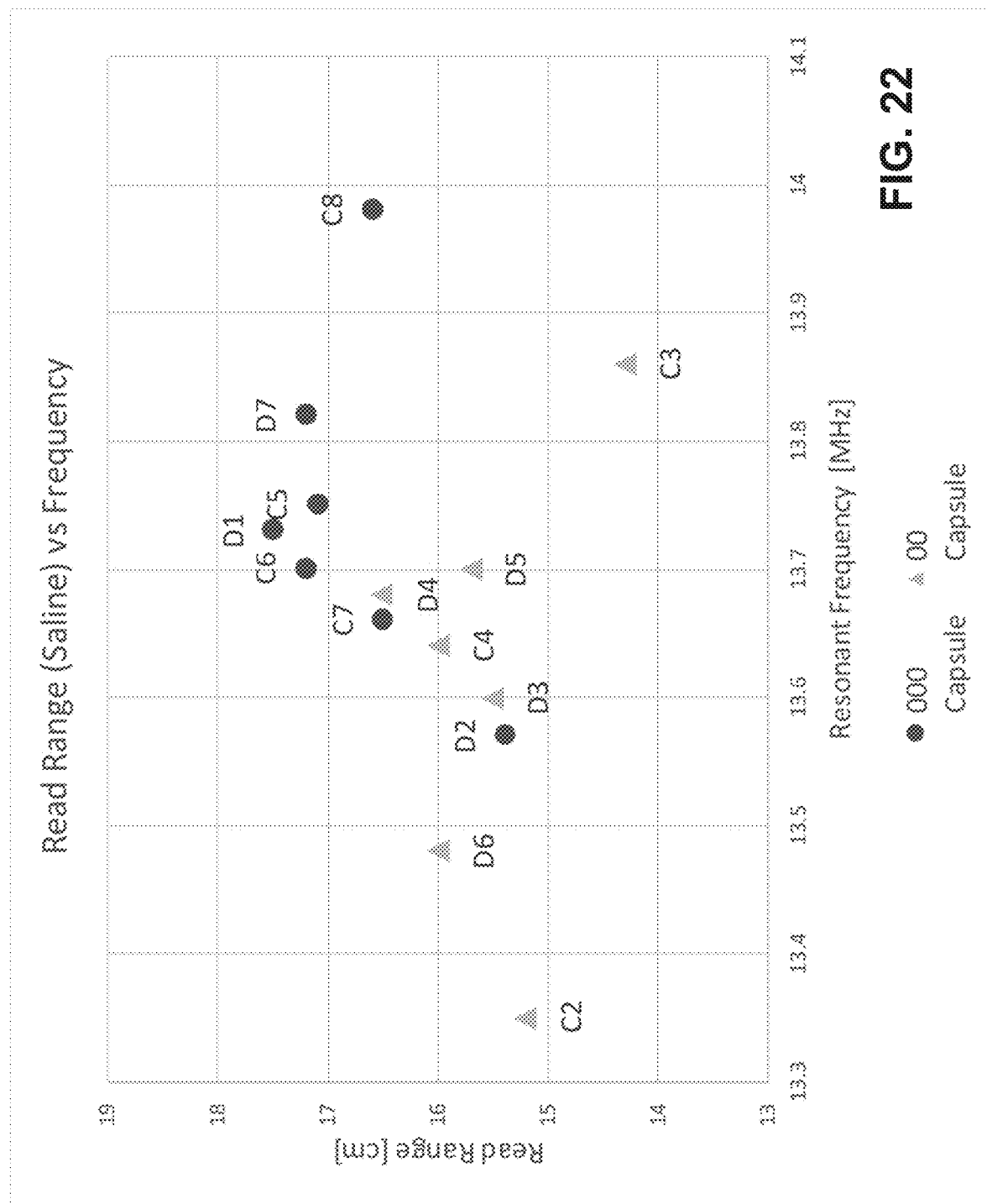

INGESTIBLE RFID TAG AND READER SYSTEM

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 U.S.C. § 119(e) for provisional patent applications, for any and all parent, grandparent, great-grandparent, etc. applications of the Priority Application(s)).

PRIORITY APPLICATIONS

The present application claims the benefit under 35 U.S.C. § 119(e) of United States Provisional Patent Application No. 62/791,085, entitled INGESTIBLE RFID TAG AND READER SYSTEM, naming MARK S. FREEMAN, FRIDRIK LARUSSON, STEVEN A. RODRIGUEZ, and LOWELL L. WOOD, JR. as inventors, filed 11 Jan. 2019, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a radio frequency identification (RFID) tag includes, but is not limited to, a flexible substrate having a first portion and a second portion extending from the first portion, the first portion foldable between a planar configuration and a tubular configuration, the second portion foldable between a planar configuration and a folded configuration; a conductive element disposed at least on a first side of the first portion of the flexible substrate; and an RFID tag chip disposed at least on a first side of the second portion of the flexible substrate.

In an aspect, a system includes, but is not limited to, an RFID tag structured and dimensioned for ingestion by a biological subject, the RFID tag including a flexible substrate having a first portion and a second portion extending from the first portion, the first portion foldable between a planar configuration and a tubular configuration, the second portion foldable between a planar configuration and a folded configuration, a conductive element disposed at least on a first side of the first portion of the flexible substrate, and an RFID tag chip disposed at least on a first side of the second portion of the flexible substrate; and an RFID reader including a coil structured and dimensioned to interrogate the RFID tag within the biological subject.

In an aspect, a system includes, but is not limited to, an RFID tag including a flexible substrate having a first portion and a second portion extending from the first portion, the first portion foldable between a planar configuration and a tubular configuration, the second portion foldable between a planar configuration and a folded configuration, a conductive element disposed at least on a first side of the first portion of the flexible substrate, and an RFID tag chip disposed at least on a first side of the second portion of the flexible substrate; a capsule structured and dimensioned for ingestion by a biological subject, the capsule including a shell structured and dimensioned to enclose the RFID tag when the first portion of the flexible substrate is in the tubular configuration, but not when the first portion of the flexible substrate is in the planar configuration; and an RFID reader including a coil structured and dimensioned to interrogate the RFID tag within the biological subject.

In an aspect, a system includes, but is not limited to, an RFID tag including a flexible substrate foldable between a planar configuration and a tubular configuration, a conductive element disposed at least on a first side of the flexible substrate, and an RFID tag chip disposed at least on the first side of the flexible substrate electrically coupled with the conductive element; a capsule structured and dimensioned for ingestion by a biological subject, the capsule including a shell structured and dimensioned to enclose a medication for the biological subject simultaneously with the RFID tag when the flexible substrate is in the tubular configuration, but not when the flexible substrate is in the planar configuration; and a pH switch structure coupled to an exterior surface of the capsule, the pH switch configured to deactivate the RFID tag in a first configuration of the pH switch structure and to permit activation of the RFID tag in a second configuration of the pH switch structure within the biological subject.

In an aspect, a system includes, but is not limited to, an RFID tag including a flexible substrate foldable between a planar configuration and a tubular configuration, a conductive element disposed at least on a first side of the flexible substrate, and an RFID tag chip disposed at least on the first side of the flexible substrate electrically coupled with the conductive element; a capsule structured and dimensioned for ingestion by a biological subject, the capsule including a shell structured and dimensioned to enclose a medication for the biological subject simultaneously with the RFID tag when the flexible substrate is in the tubular configuration, but not when the flexible substrate is in the planar configuration; a pH switch structure coupled to an exterior surface of the capsule, the pH switch configured to deactivate the RFID tag in a first configuration of the pH switch structure and to permit activation of the RFID tag in a second configuration of the pH switch structure within the biological subject; and an RFID reader including a coil structured and dimensioned to interrogate the RFID tag within the biological subject.

In an aspect, a system includes, but is not limited to, a capsule structured and dimensioned for ingestion by a biological subject, the capsule including a shell structured and dimensioned to enclose a medication for the biological subject simultaneously with the RFID tag; the RFID tag including a flexible substrate formed in a structure for positioning within the capsule, a conductive element disposed at least on a first side of the flexible substrate, and an RFID tag chip disposed at least on a second side of the flexible substrate; and a pH switch structure coupled to an exterior surface of the capsule, the pH switch configured to deactivate the RFID tag in a first configuration of the pH switch structure and to permit activation of the RFID tag in a second configuration of the pH switch structure within the biological subject.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 14 is a table of read range measurements in air or saline for different orientations of an embodiment of an RFID reader relative to different configurations of ingestible RFID tags in planar and tubular configurations.

FIG. 17 is a chart of read range measurements in air for different RFID antenna and RFID reader configurations relative to an ingestible RFID tag.

FIG. 18 is a table of experimental conditions for a series of bench experiments to determine the read range of different RFID tag configurations and RFID reader configurations.

FIG. 22 is a chart of measured read ranges versus resonant frequency in saline for various capsule types from example experiments.

DETAILED DESCRIPTION

Figure 1:
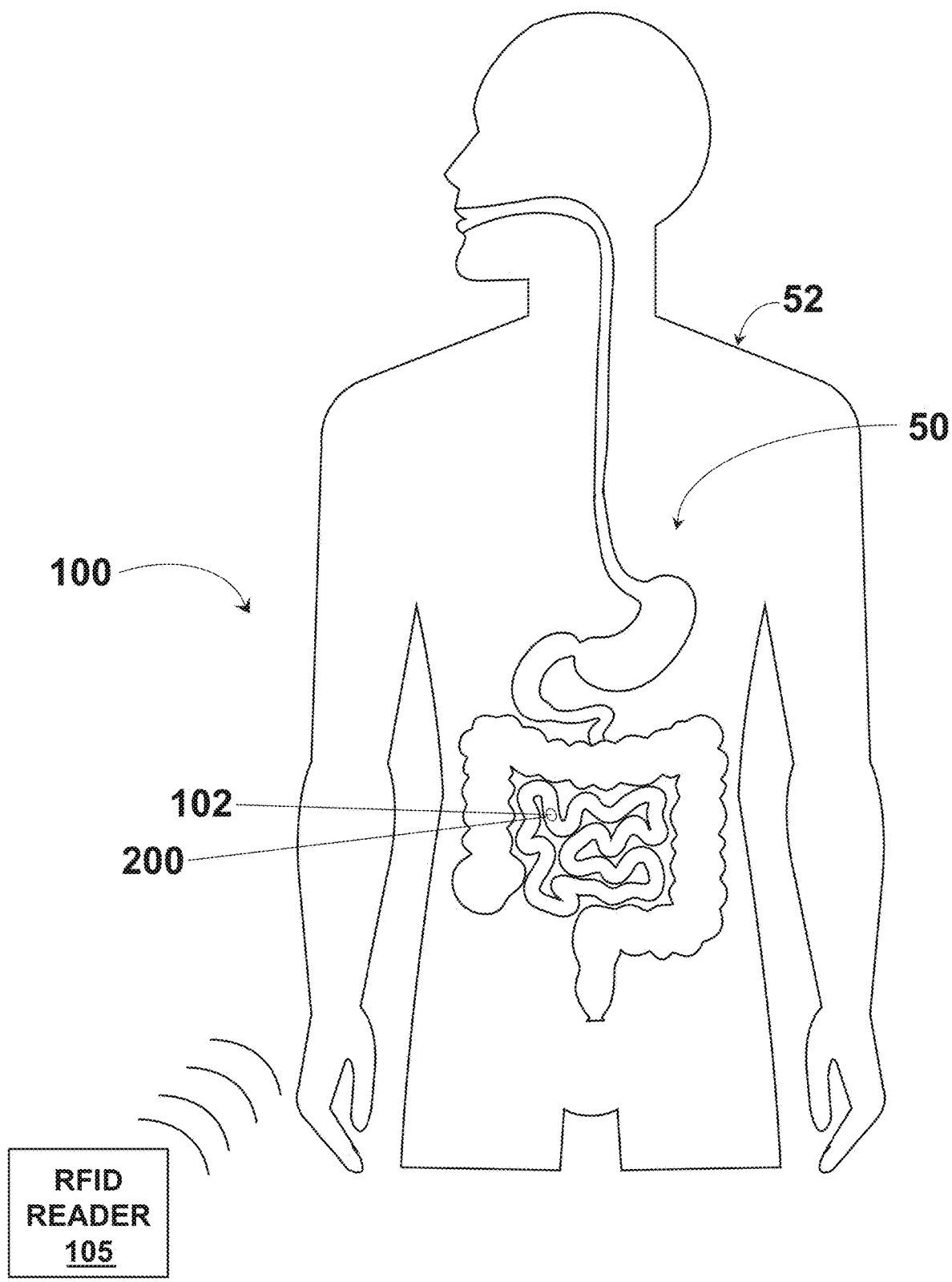
FIG. 1 is a schematic illustration of an ingestible RFID system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems are described herein for ingestible radio frequency identification (RFID) tags, which can be utilized for tracking adherence of patients to medication protocols. For certain disease states, a patient may be directed to adhere to a medication course involving ingestion of multiple dosages per day, ingestion of multiple different drug capsules per day, ingestion of medication for multiple days, or combinations thereof. For example, treatment of tuberculosis or other infectious diseases can involve multiple doses of antibiotics over the course of multiple weeks or months. Patient compliance with a medication course can decline with long courses or complex dosages of medication. Other times, as a patient begins to feel short term benefits of the medication course, the patient may fail to complete the medication course, which can lead to failure to fully treat a disease, a risk of resurgence of the disease or disease symptoms, activation of latent bacteria, or the like. In some instances, patients may be motivated to sell the medication rather than use it for treatment of a condition as prescribed. For instance, a patient may attempt to feign taking the medication only to remove the medication from the treatment facility without ingestion.

Systems described herein include ingestible RFID tags to accompany medication as it is ingested by a patient, and associated readers positioned external to the patient to register the presence of the ingestible RFID tag within the patient, or lack thereof. These systems can be utilized by medical personnel to confirm ingestion of oral medications, for example to confirm compliance with a specific and prescribed medication regimen. The ingestible RFID tags incorporate a flexible substrate that can facilitate transition between a planar state and a cylindrical or tubular state. RFID tags in the tubular state can be positioned within a capsule (e.g., a gel-based capsule, a synthetic polymer-based capsule, etc.) while allowing space for medication within the capsule, such as within an internal region of the RFID tags in the tubular state. The flexible substrate can include a first portion for positioning of an RFID tag coil and a second portion for positioning of RFID tag chip hardware. The second portion of the flexible substrate extends from the first portion to provide a relatively large surface area for the RFID tag coil on the first portion, while retaining a form factor suitable for insertion within a medication capsule. In some embodiments, the flexible substrate includes the RFID tag chip hardware and the RFID tag coil on the same portion of the flexible substrate.

The systems described herein can include mechanisms to verify that a medication has been ingested by a patient within a recent time period. Such mechanisms can prevent detection of the RFID tag when the RFID tag is present in an environment outside the patient and permit detection when the RFID tag is present within the patient (e.g., in the stomach). For example, the RFID tag can be positioned within a capsule (e.g., in a tubular state within the capsule interior) and the capsule can include a pH switch structure that utilizes a change in pH between the environment external to the patient and the environment internal to the patient (e.g., the digestive system) to permit detection of the RFID tag within the patient. In some embodiments, the pH switch structure is coupled to an exterior surface of the capsule to shield or otherwise interfere with communications between the RFID tag within the capsule and an external RFID reader. The pH switch structure can transition between structural states in response to exposure to a specific pH range (e.g., a pH range associated with a stomach or stomach acid) to reduce shielding or mitigate interference with communications between the RFID tag within the capsule and the external RFID reader to permit identification of the RFID tag within the patient. For example, the pH switch structure can include a biocompatible metal that reacts with hydrochloric acid in the stomach to dissolve at least a portion of the pH switch structure when in the stomach and that remains intact when outside the patient.

Referring to FIGS. 1-4, an example system 100 for providing an ingestible RFID tag with an associated reader is shown, which can serve as context for one or more devices and/or systems described herein. The system 100 includes an RFID tag 102 having a size and shape for introduction to a digestive system 50 of an individual subject 52, such as through ingestion of the RFID tag 102 by the individual subject 52. The RFID tag 102 includes an architecture that incorporates conductive element coils that can be rolled into a cylindrical or tubular form and associated with a medication, such as being placed within a medication capsule, being formed with medicine as a medication tablet or capsule, or the like. In some embodiments, the RFID tag 102 is manufactured as a flexible tubular structure, such as with 3D printing. In some embodiments, the RFID tag 102 is manufactured as a flexible planar structure which is then rolled or folded into a cylindrical or tubular form and associated with a medication. For example, the RFID tag 102 includes a flexible substrate 104 that is foldable between a planar configuration (e.g., shown in FIG. 4) and a folded or tubular configuration (e.g., shown in FIG. 2). The flexible substrate 104 can include, but is not limited to, a polyimide material, a polyester film material (e.g., stretched polyethylene terephthalate ("Mylar")), or other material to facilitate reversible folding between the planar configuration and the folded or tubular configuration. The conductive element coils can be positioned, etched, printed, or otherwise formed on a single side of the flexible substrate 104 or on multiple sides of the flexible substrate 104. The flexible substrate 104 facilitates introduction of the RFID tag 102 into a capsule 200 when in the folded or tubular configuration to accompany medication within the capsule for ingestion by the individual subject 52. The system 100 includes an RFID reader 105 to identify the presence of the RFID tag 102 within the individual subject 52 through radio frequency interrogation. The system 100 can be utilized with human subjects (e.g., individual subject 52) or non-human subjects (e.g., domesticated or non-domesticated animals) to introduce the RFID tag 102 to the subject, which can be utilized to track compliance with medication protocols.

Figure 4:
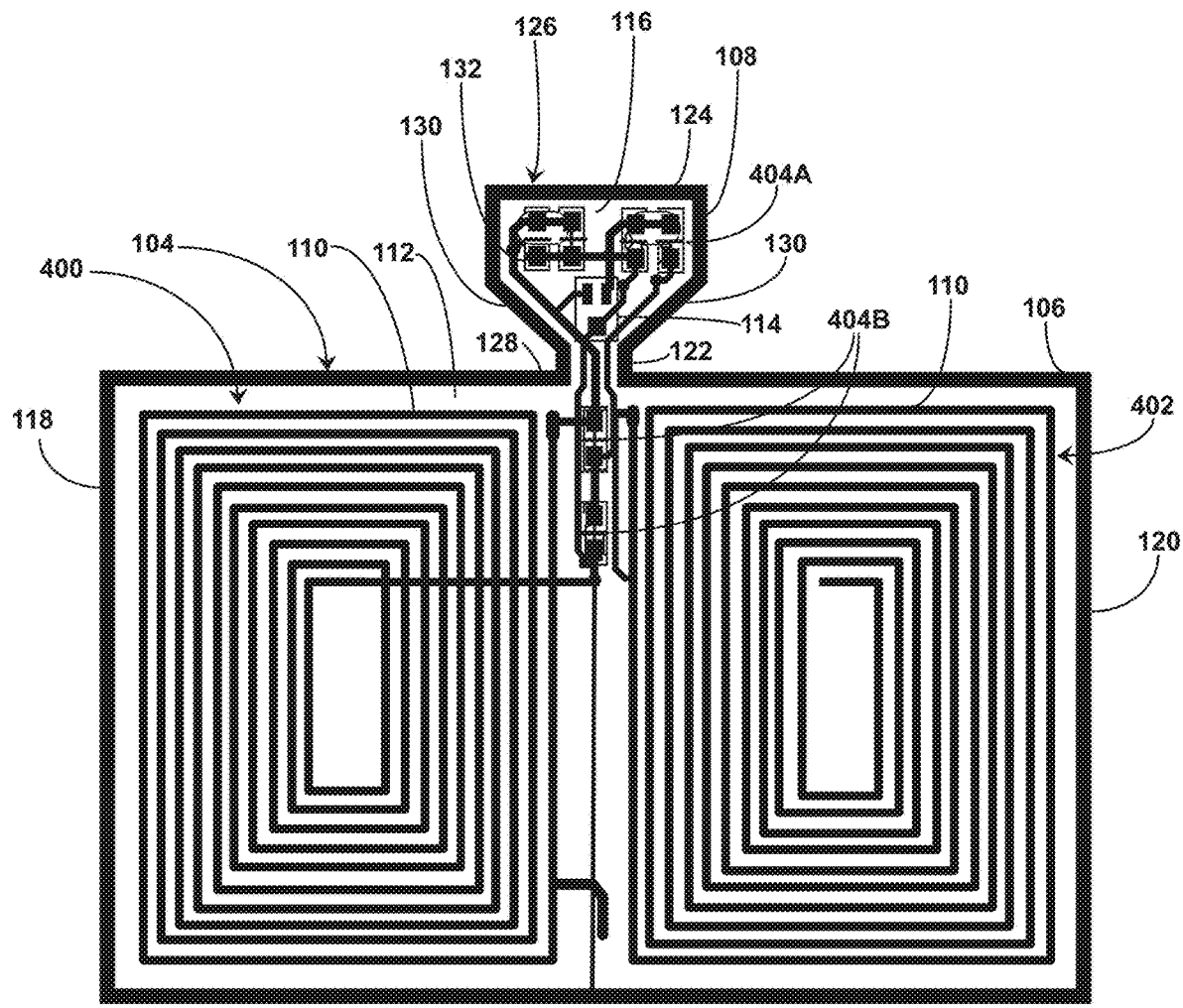
FIG. 4 illustrates a top view of an embodiment of an ingestible RFID tag in a planar configuration with rectangular conductive elements.

Referring to FIG. 4, an example RFID tag 102 is shown in a planar configuration. The RFID tag 102 includes the flexible substrate 104, where the flexible substrate 104 includes at least two portions: a first portion 106 and a second portion 108 extending from the first portion 106. The first portion 106 provides a relatively large surface area to support a conductive element 110 arranged in a rectangular coil pattern on at least a first side 112 of the first portion 106. The conductive element 110 can include a metallic material, such as a metallic foil. In some embodiments, the conductive element 110 includes a copper material, such as a copper foil. In some embodiments, the conductive element 110 includes a screen-printed conductor. In some embodiments, the flexible substrate 104 includes a polyester film substrate (e.g., stretched polyethylene terephthalate ("Mylar")) with silver ink conductors as the conductive element 110 on and/or in the polyester film. The second portion 108 supports an RFID tag chip 114 on a first side 116 of the second portion 108. The first portion 106 is foldable between a planar configuration (e.g., shown in FIG. 4) and a tubular configuration (e.g., shown in FIG. 2) to facilitate introduction of the RFID tag 102 into the capsule 200. For example, the first portion 106 includes a first end 118 and a second end 120 opposing the first end 118, where the first end 118 is positioned adjacent the second end 120 when the first portion 106 is in the tubular configuration. In some embodiments, the first end 118 is not coupled to the second end 120 when the first portion 106 is in the tubular configuration. For example, a gap or spacing between the first end 118 and the second end 120 can be present when the first portion 106 is in the tubular configuration. Alternatively or additionally, the first end 118 and the second end 120 can at least partially overlap when the first portion 106 is in the tubular configuration. In some embodiments, the second portion 108 has a surface area that is less than a surface area of the first portion 106. For instance, the surface area occupied by the conductive element 110 in the coil pattern can be larger than the surface area occupied by the RFID tag chip 114 and other devices or objects positioned on the second portion 108.

In some embodiments, the second portion 108 of the flexible substrate 104 includes a narrow segment 122 coupled to and extending from the first portion 106. The narrow segment 122 extends into a tab segment 124 having a wider surface area than the narrow segment 122. In some embodiments, the narrow segment 122 has a surface area that is less than a surface area of the tab segment 124. The second portion 108 of the flexible substrate 104 is structured and dimensioned to bend at least at the narrow segment 122 when transitioned from the planar configuration (e.g., shown in FIG. 4) to the folded configuration (e.g., shown in FIG. 2). For example, a top side 126 of the tab segment 124 can be brought into position closer to the first portion 106 of the flexible substrate 104 when the second portion 108 of the flexible substrate 104 is in the folded configuration than when in the planar configuration. In some embodiments, the RFID tag chip 114 is disposed on the tab segment 124, which can facilitate bending about the narrow segment 122 to transition the second portion 108 between the planar configuration and the folded configuration.

Figure 2:
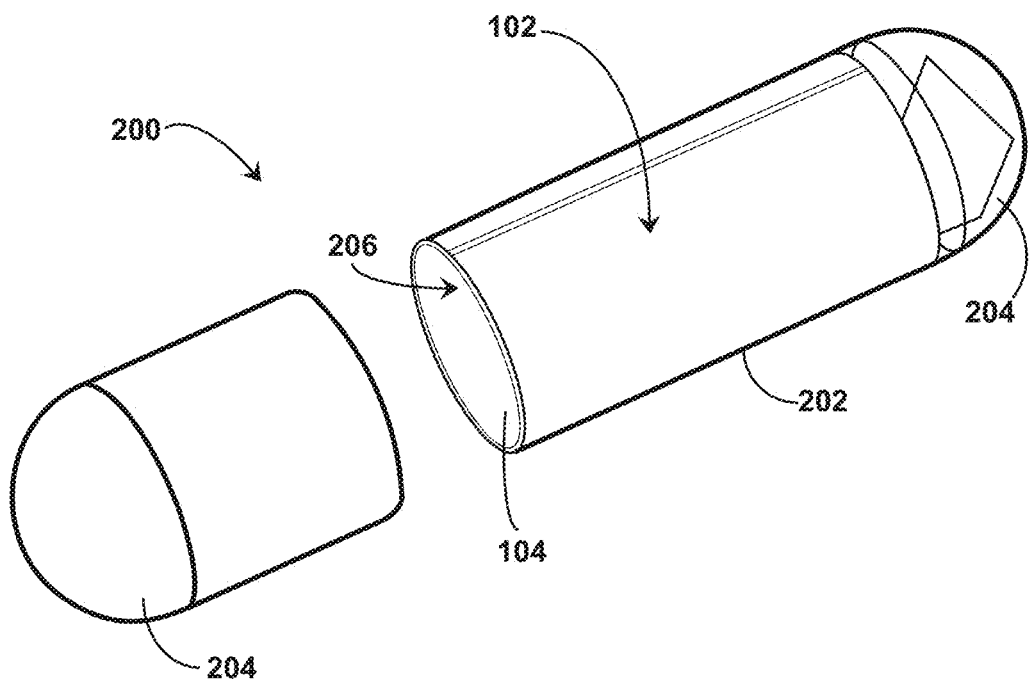
FIG. 2 illustrates an isometric view of an ingestible RFID tag in a tubular configuration positioned within a capsule.

The folded configuration of the second portion 108 of the flexible substrate 104 can facilitate introduction of the RFID tag 102 into the capsule 200. For example, as shown in FIG. 2, the capsule 200 can include a tubular shell 202 having opposing end caps 204. The capsule 200 is structured and dimensioned to enclose the RFID tag 102 when the first portion 106 of the flexible substrate 104 is in the tubular configuration, but not when the first portion 106 of the flexible substrate 104 is in the planar configuration. The tubular shell 202 can enclose at least a portion of the first portion 106 of the flexible substrate 104 when the first portion 106 is in the tubular configuration. For example, as shown in FIG. 2, the tubular shell 202 encloses the first portion 106 of the flexible substrate 104 in the tubular configuration in an interior region 206 of the tubular shell 202 while the second portion 108 extends into the end cap 204 in the folded configuration. In some embodiments, the end cap 204 is structured and dimensioned to enclose the second portion 108 in an interior region 208 of the end cap 204 when the second portion 108 is in the folded configuration, but not when the second portion 108 is in the planar configuration. For example, by positioning the RFID tag chip 114 on the tab segment 124, the interior region 208 of the end cap 204 can enclose the second portion 108 of the flexible substrate 104 while allowing the majority of the first portion 106 to be dedicated to coil configurations of the conductive elements 110, which can be enclosed in the capsule 200 by the tubular shell 202.

In some embodiments, the flexible substrate 104 is a continuous substrate where the first portion 106 and the second portion 108 are formed from the same substrate material as a single piece construction. In some embodiments, the first portion 106 and the second portion 108 are formed from separate substrate pieces and fused, adhered, or otherwise coupled together, such as through a coupling of the narrow segment 122 of the second portion 108 to a top side 128 of the first portion 106.

Figure 5:
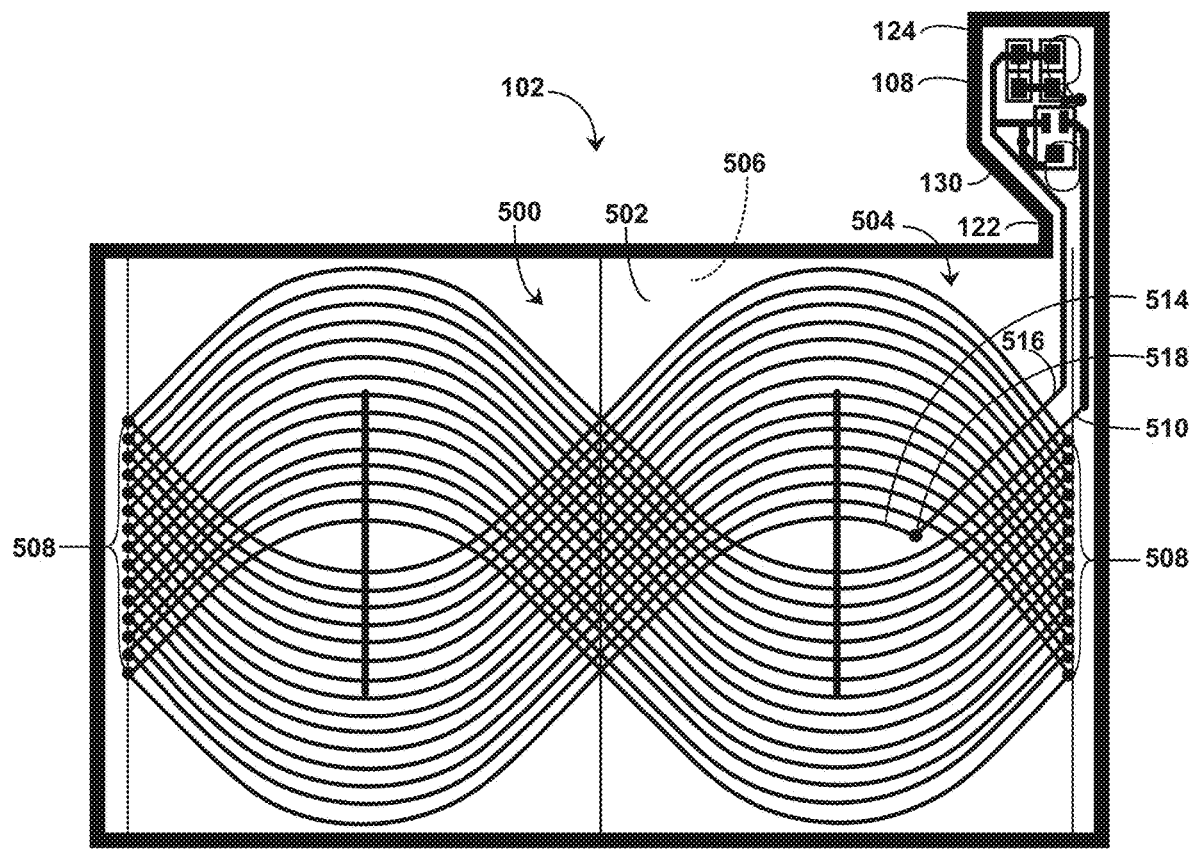
FIG. 5 illustrates a top view of an embodiment of an ingestible RFID tag in a planar configuration with sinusoidal conductive elements.
Figure 6A:
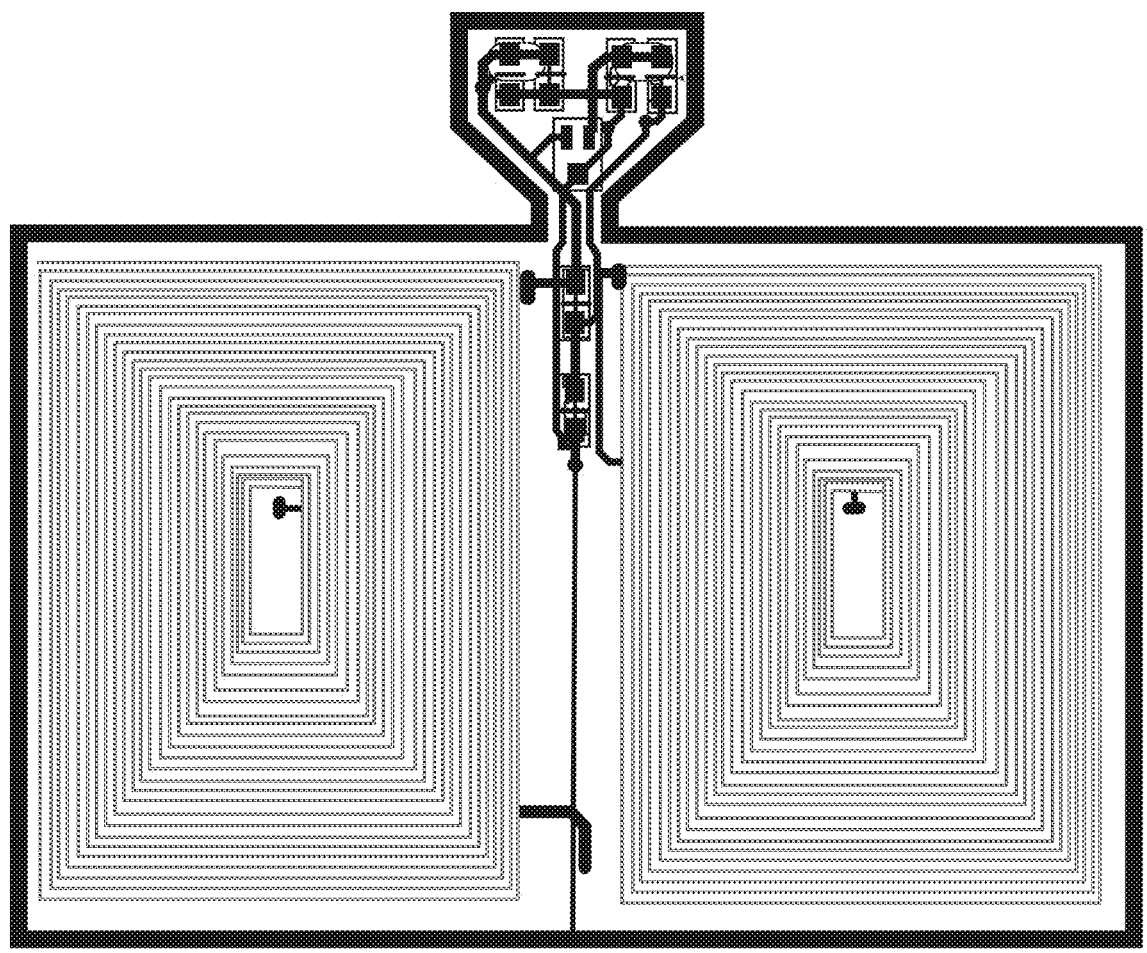
FIG. 6A illustrates a top view of an embodiment of an ingestible RFID tag in a planar configuration.
Figure 6B:
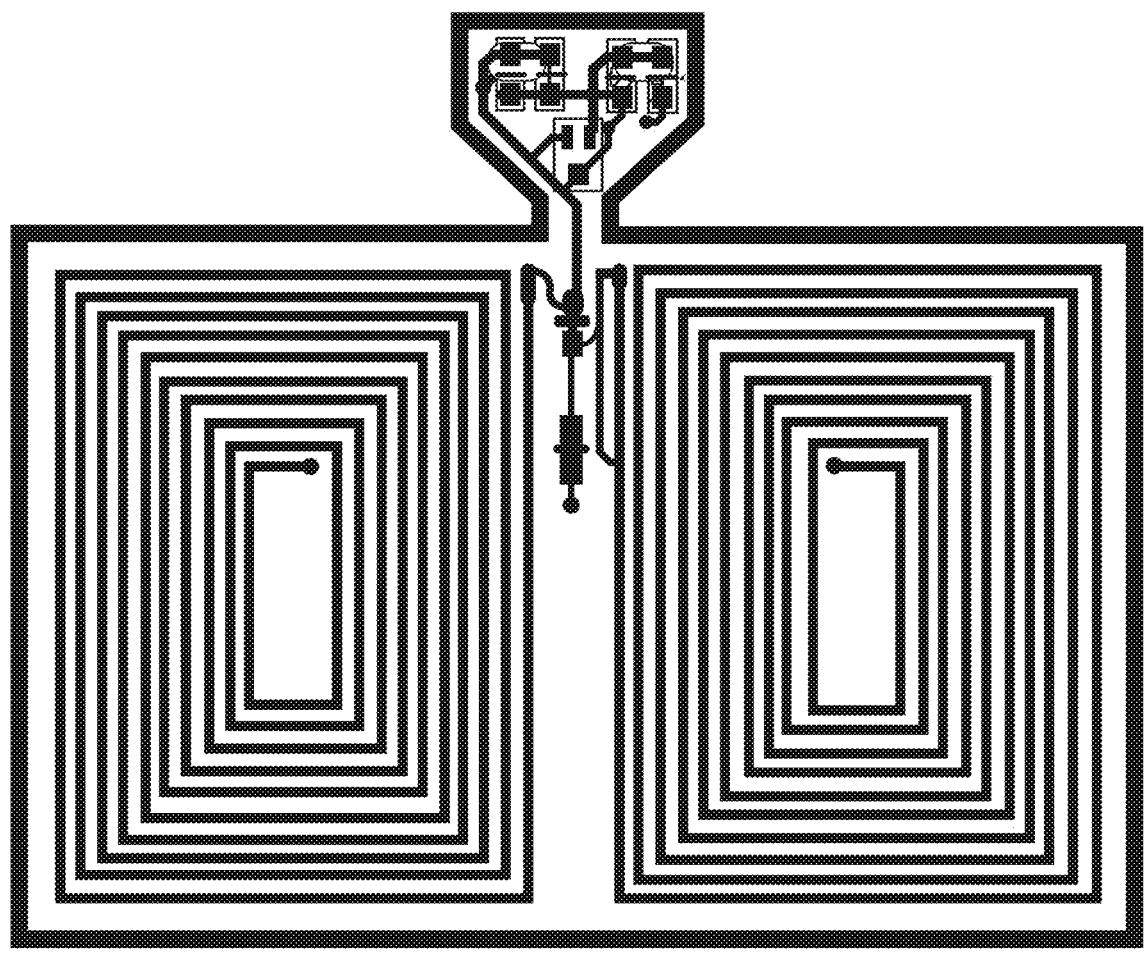
FIG. 6B illustrates a top view of an embodiment of an ingestible RFID tag in a planar configuration.
Figure 6C:
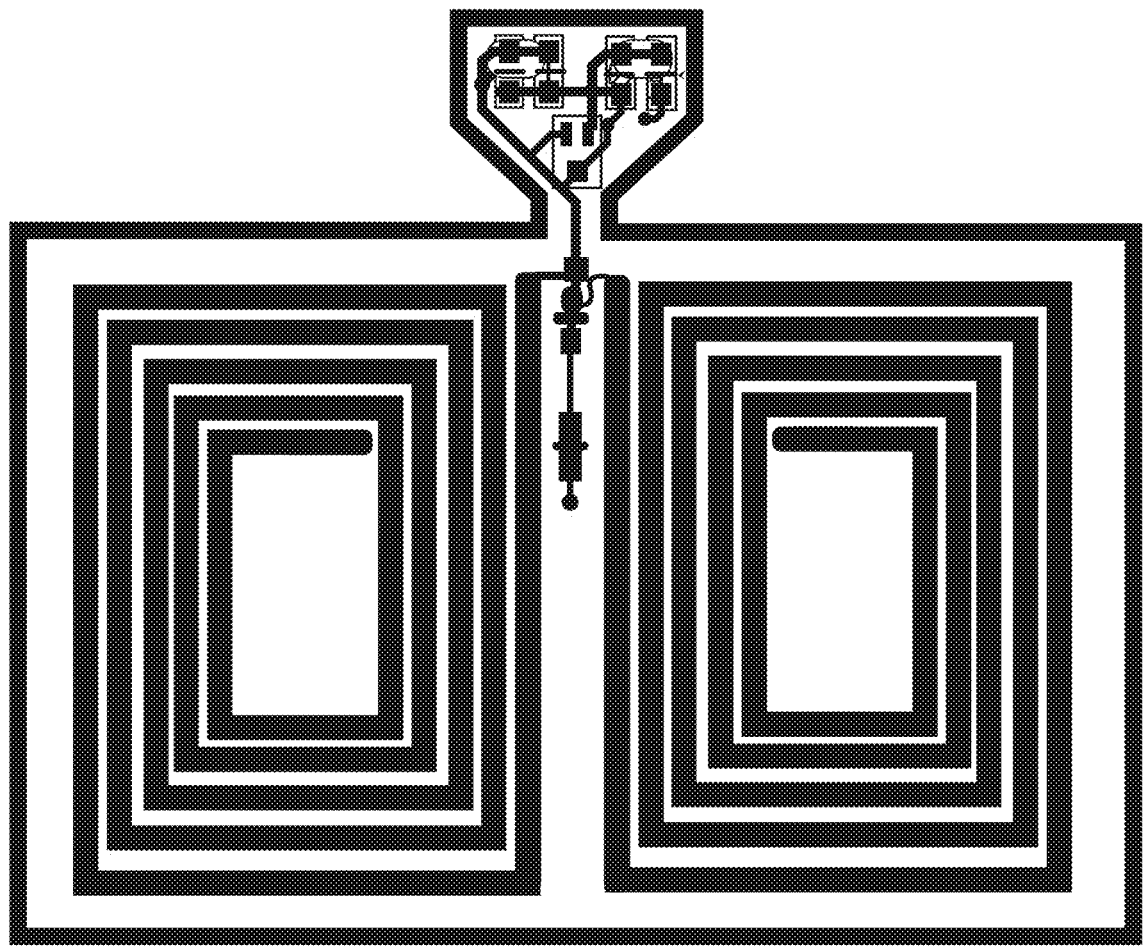
FIG. 6C illustrates a top view of an embodiment of an ingestible RFID tag in a planar configuration.
Figure 6D:
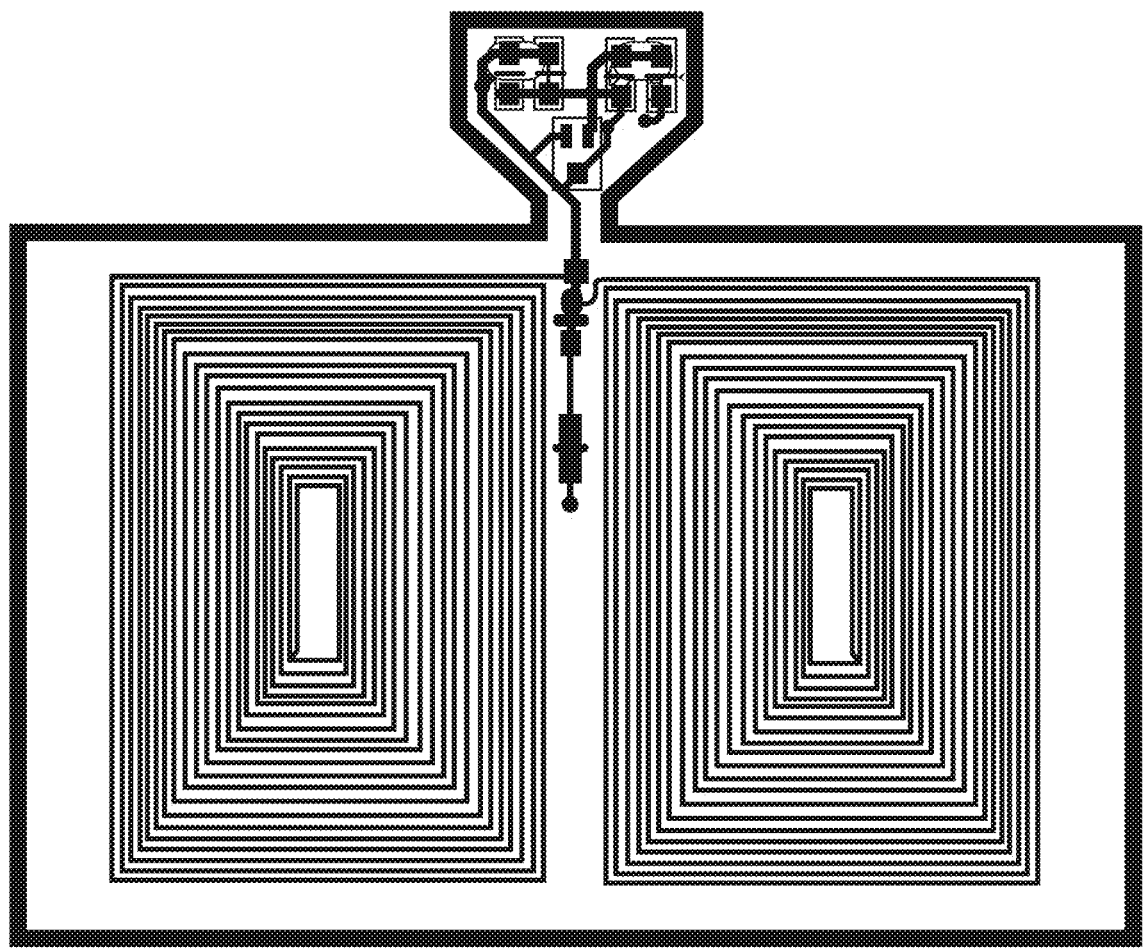
FIG. 6D illustrates a top view of an embodiment of an ingestible RFID tag in a planar configuration.
Figure 6E:
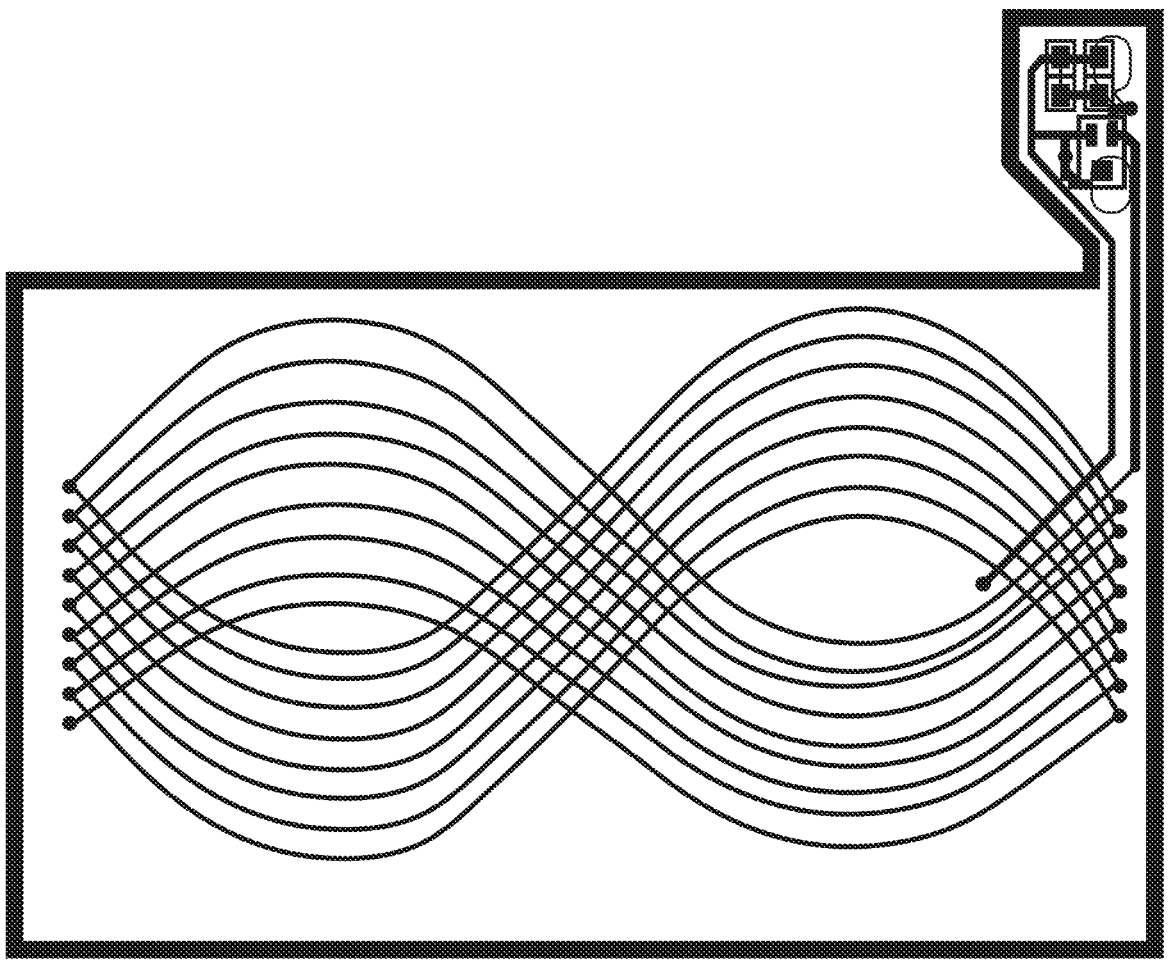
FIG. 6E illustrates a top view of an embodiment of an ingestible RFID tag in a planar configuration.

The tab segment 124 of the second portion 108 of the flexible substrate 104 can include one or more tapers (e.g., tapered edges) to couple the tab segment 124 to the narrow segment 122. For example, FIG. 4 shows an example RFID tag 102 that includes two opposing tapers 130. Additional example RFID tags 102 including two opposing tapers 130 are shown in FIGS. 6A, 6B, 6C, and 6D. FIG. 5 shows an example RFID tag 102 that includes one taper 130 that couples the tab segment 124 to the narrow segment 122. An additional example RFID tag 102 including one taper 130 is shown in FIG. 6E. In some embodiments, the tab segment 124 supports one or more tuning capacitors 132 for the RFID tag 102.

The RFID reader 105 communicates with the RFID tag 102 with radio frequency signals. In the use case wherein the RFID tag 102 is scanned while internal to an individual (e.g.

for medication compliance), the radio frequency signals should be sufficient for this communication while still medically safe for the individual. In some embodiments, the RFID reader 105 includes a coil structured and dimensioned to generate communication signals having low frequency (e.g., on the order of 100 kHz) or high frequency signals (e.g., 13.56 MHz). In some embodiments, the coil has a width of approximately 9 cm. In some embodiments, the coil has a width of approximately 17.8 cm. However, the RFID reader 105 is not limited to the frequencies or widths provided herein and can operate with frequencies between 100 kHz and 13.56 MHz or frequencies greater than 13.56 MHz, and can include a coil having a width of less than 9 cm, between 9 and 17.8 cm, or greater than 17.8 cm.

Figure 6F:
FIG. 6F illustrates an isometric view of an embodiment of an ingestible RFID tag in a tubular configuration.

Referring to FIG. 4, the example RFID tag 102 has the conductive element 110 formed into a substantially rectangular coil having a plurality of turns disposed on the first side 112 of the first portion 106 of the flexible substrate 104. For the example RFID tag 102 in FIG. 4, the coil configuration includes ten turns, however other numbers of turns can be utilized. For example, the plurality of turns can be from five turns to twenty-five turns to accommodate capsule sizes of up to size 000 capsules. The width of the conductive element 110 used to make the coil can affect the number of turns available for a given RFID tag 102, dependent on the size of capsule 200 into which the RFID tag 102 is to be introduced. For example, a thicker conductive element 110 can be used for fewer turns as compared to a thinner conductive element 110 (e.g., comparing the RFID tag 102 of FIG. 4 with the RFID tag of FIG. 6A). In some embodiments, the spacing between turns of the conductive elements is three-thousands of an inch spacing between turns. FIG. 6A shows an example RFID tag 102 having a coil configuration with twenty-five turns. FIG. 6B shows an example RFID tag 102 having a coil configuration with ten turns. FIG. 6C shows an example RFID tag 102 having a coil configuration with five turns. FIG. 6D shows an example RFID tag 102 having a coil configuration with twenty turns. The conductive element 110 can include multiple coil configurations on the first side 112 of the first portion 106 of the flexible substrate 104. For example, the example RFID tag 102 of FIG. 4 includes a first coil configuration 400 on the first side 112 of the first portion 106 and a second coil configuration 402 opposing the first coil configuration 400 on the first side 112 of the first portion 106. In some embodiments, the first coil configuration 400 includes the same number of turns as the second coil configuration 402. For example, in FIG. 4, the first coil configuration 400 and the second coil configuration 402 each includes ten turns of the conductive element 110. The RFID tag can also include a jumper set connecting the first coil configuration 400 and the second coil configuration between serial and parallel connections (jumper sets 404A and 404B are shown in FIG. 4). The number and positioning of coils can vary based on the particular application of the RFID tag 102. For example, FIG. 6F shows an example RFID tag 102 having four coils positioned around the circumference of the flexible substrate 104 when in a tubular configuration.

The RFID tag 102 can include conductive elements 110 on both sides of the deformable substrate 104 (e.g., a front surface and a rear surface) to form an RFID antenna. Referring to FIG. 5, the example RFID tag 102 has the conductive element 110 formed into a first sinusoidal pattern 500 on a first side 502 of the first portion 106 of the deformable substrate 104 and the conductive element 110 formed into a second sinusoidal pattern 504 on a second side 506 of the first portion 106 of the deformable substrate 104.

Figure 3:
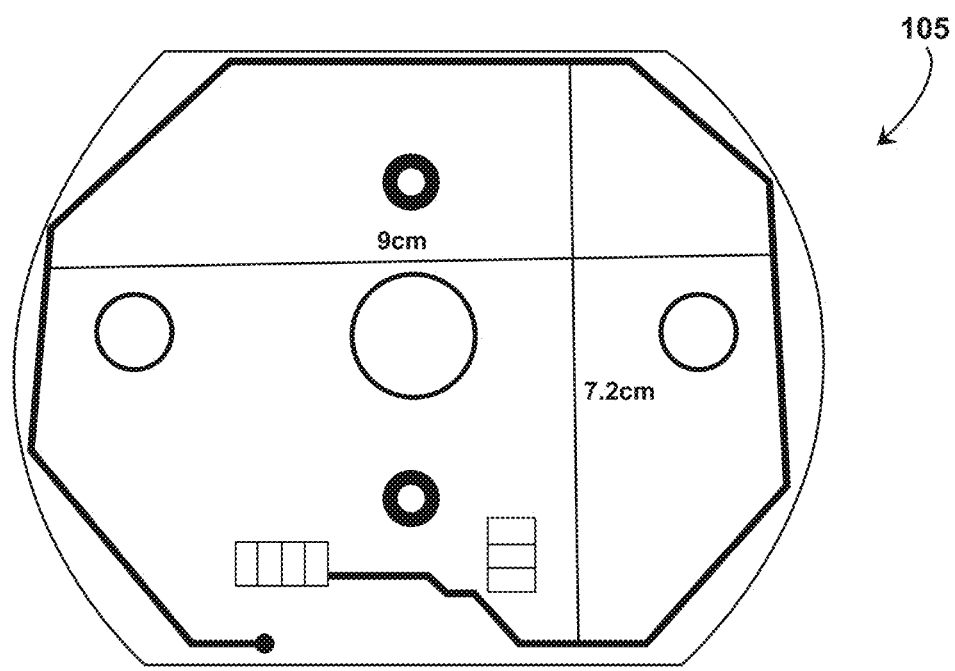
FIG. 3 illustrates a top view of an embodiment of an RFID reader.

The conductive element 110 can take the shape of two helixes when the first portion 106 of the deformable substrate 104 is in the tubular configuration (e.g., shown in FIG. 3). The deformable substrate 104 is shown as transparent in FIG. 5 to show the layout of the first sinusoidal pattern 500 with respect to the second sinusoidal pattern 504. The RFID tag 102 includes a plurality of conductive vias 508 through the deformable substrate 104 to couple at least a portion of the first sinusoidal pattern 500 with at least a portion of the second sinusoidal pattern 504 (e.g., to create a continuous conductive path through each of the first sinusoidal pattern 500 and the second sinusoidal pattern 504).

In some embodiments, an end of a conductive element 110 of each of the first sinusoidal pattern 500 and the second sinusoidal pattern 504 is coupled to a trace extending from the first portion 106 of the flexible substrate 104 onto the second portion 108 of the flexible substrate 104. For example, as shown in FIG. 5, an end 510 of the conductive element 110 of the first sinusoidal pattern 500 is coupled to a trace 512 on the first side 502 of the deformable substrate 104, where the trace 512 extends from the first portion 106 of the flexible substrate 104 onto the second portion 108 of the flexible substrate 104 (e.g., to electrically connect with one or more of the RFID tag chip 114, tuning capacitors 132, or the like). Additionally, an end 514 of the conductive element 110 of the second sinusoidal pattern 504 on the second side 506 of the first portion 106 is coupled to a trace 516 on the first side 502 of the deformable substrate 104 through a via 518, where the trace 516 extends from the first portion 106 of the flexible substrate 104 onto the second portion 108 of the flexible substrate 104 (e.g., to electrically connect with one or more of the RFID tag chip 114, tuning capacitors 132, or the like). The first sinusoidal pattern 500 and the second sinusoidal pattern 504 can include the same number of turns of conductive elements 110 to form the respective patterns. For the example RFID tag 102 in FIG. 5, each of the first sinusoidal pattern 500 and the second sinusoidal pattern 504 includes fifteen turns, however other numbers of turns can be utilized. For example, the plurality of turns can be from five to fifteen turns to accommodate capsule sizes of up to 000 capsules. FIG. 6E shows an example RFID tag 102 having dual sinusoidal configurations with nine turns.

Figure 7:
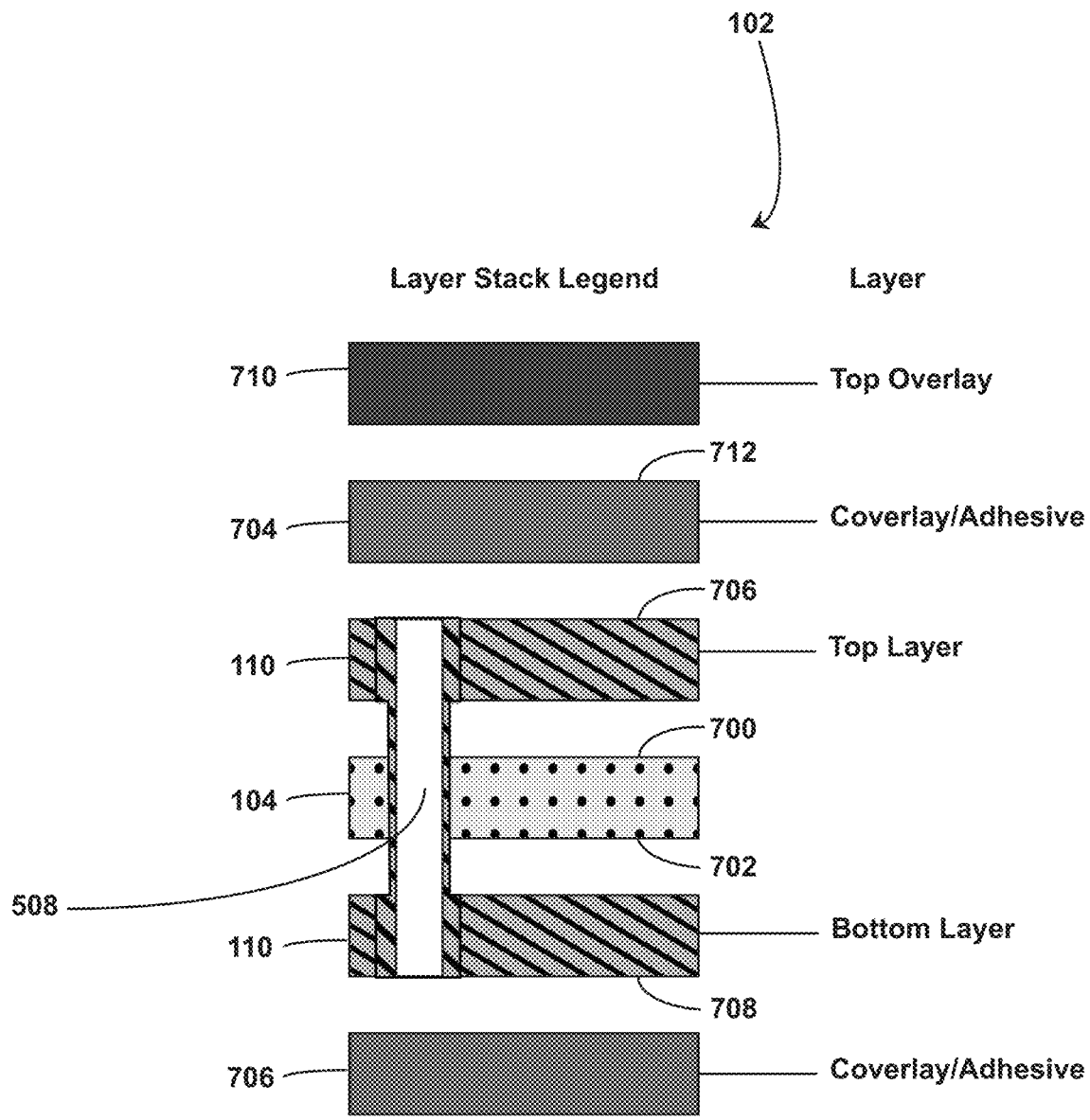
FIG. 7 illustrates a partial cross-sectional exploded view of an ingestible RFID tag in a planar configuration.

Referring to FIG. 7, a cross-section of an example ingestible RFID tag 102 in a planar configuration is shown. The RFID tag 102 includes the deformable substrate 104 having conductive elements 110 on opposing sides of the deformable substrate 104. The conductive elements 110 include a top layer disposed on a first side 700 of the deformable substrate 104, which can correspond to the first side 112, the first side 116, the first side 502, for example. The conductive elements also include a bottom layer disposed on a second side 702 of the deformable substrate 104, which can correspond to the second side 506 or a side of the deformable substrate 104 opposing the first side 112, the first side 116, or the like. The RFID tag 102 also includes a via (e.g., via 508) through the deformable substrate 104, the top layer, and the bottom layer, to electrically connect the conductive elements 110 of the top layer and the bottom layer. In the example shown in FIG. 7, the deformable substrate 104 is composed of polyimide having a thickness of 0.025 mm and the conductive elements 110 of the top layer and bottom layer each have a thickness of 0.012 mm. The conductive elements 110 can be covered for protection or isolation from the external environment. For example, the RFID tag 102 includes a top coverlay and adhesive layer 704 disposed on a top surface 706 of the top layer and a bottom coverlay and adhesive layer 708 disposed on a bottom surface of the bottom layer. In embodiments, the top coverlay and adhesive layer 704 and the bottom coverlay and adhesive layer 708 each include a 0.025 mm thick polyimide coverlay and a 0.025 mm thick adhesive layer. The RFID tag 102 can also include a top overlay 710 positioned on a top surface of the top coverlay and adhesive layer 704. In some embodiments, the RFID tag 102 includes surface pads having an electroless nickel immersion gold (ENIG) finish.

Operation of ingestible RFID tags can be affected by stomach or digestive fluids. While body tissues and fluid are substantially transparent to the magnetic signals sent between an RFID tag and RFID reader, between each turn of the conductive element coil is an electric field that extends outside the plane of the coil. The electric field should be kept separate from the stomach or digestive fluids to avoid negatively affecting the performance of the coil. In some embodiments, spacing between the coil of the RFID tag 102 and the stomach or digestive fluids is provided through thickness of the capsule 200 into which the RFID tag 102 is inserted, thickness of the coverlay layers or deformable substrate 104 (described with reference to FIG. 7), or combinations thereof.

Figure 8A:
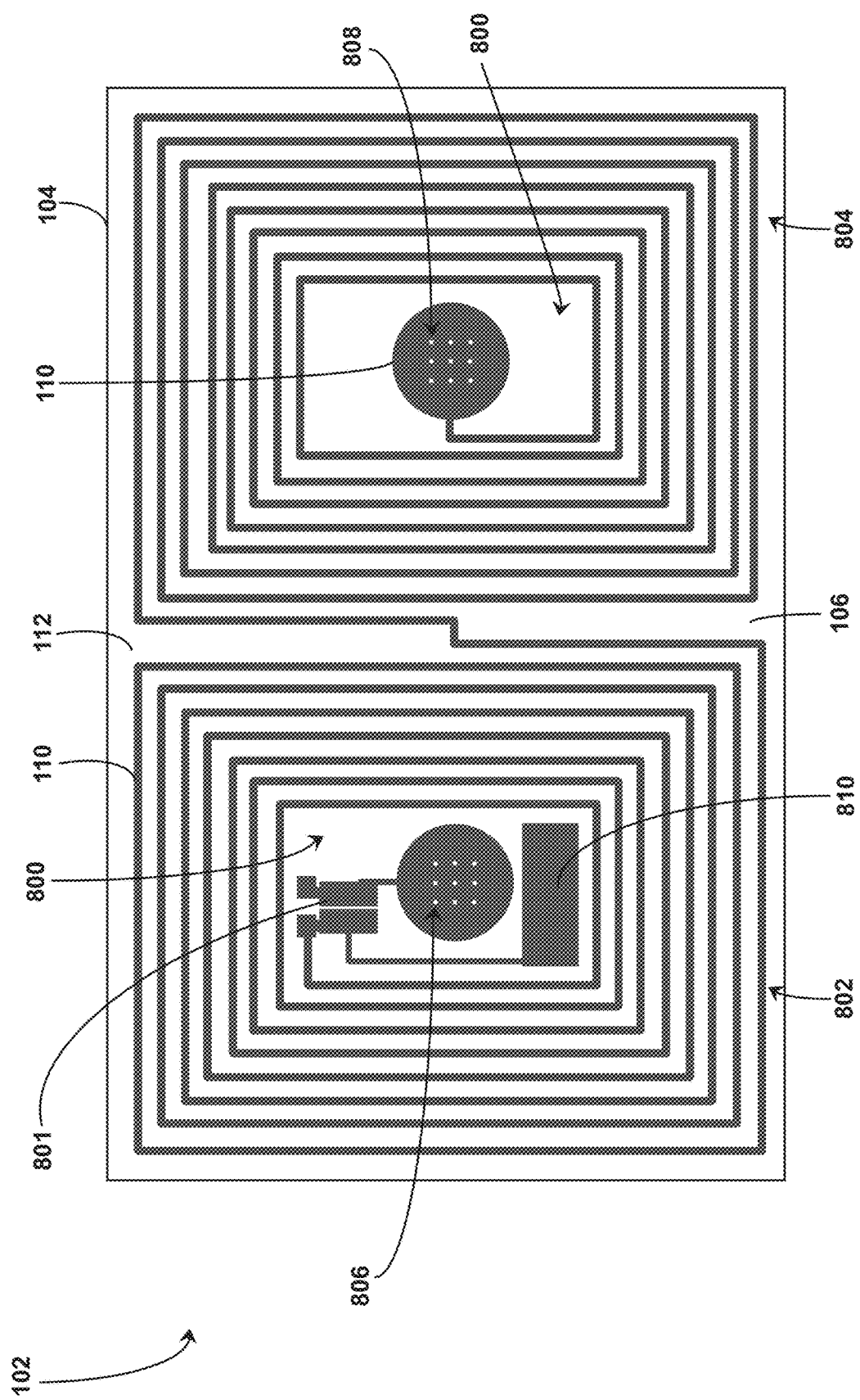
FIG. 8A illustrates a top view of an embodiment of an ingestible RFID tag in a planar configuration with conductive elements arranged in rectangular coil configurations.
Figure 8B:
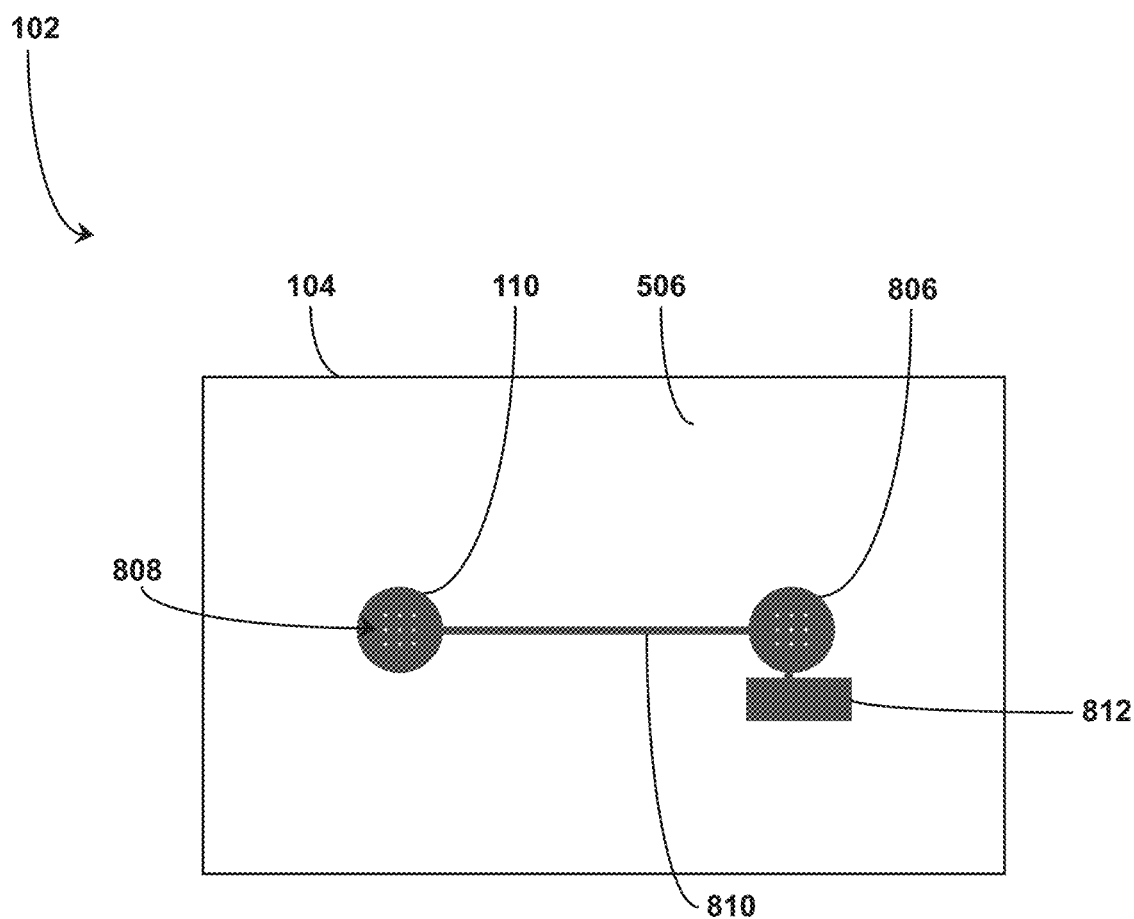
FIG. 8B illustrates a bottom view of the ingestible RFID tag of FIG. 8A.

Referring to FIGS. 8A and 8B, an example RFID tag 102 is shown in a planar configuration. The RFID tag 102 includes the flexible substrate 104 having the first portion 106 without the second portion 108 extending from the first portion 106. The RFIG tag chip hardware can be electrically coupled with the conductive elements 110 on the first portion 106. For example, FIG. 8A shows a top view of the RFID tag 102 with the conductive elements 110 disposed on the first side 112 of the flexible substrate 104. The conductive elements 110 can be arranged in a coil pattern having an interior region 800 in which the RFID tag chip hardware can be seated. For example, the RFID tag 102 is shown with the conductive elements 110 arranged in a rectangular coil pattern defining the interior region 800 on the first side 112 of the flexible substrate 104, where the RFID tag chip hardware (e.g., RFID tag chip 114) is electrically connected to the conductive elements 110 within the interior region 800 (e.g., shown in FIG. 8A as connection region 801).

Figure 15A:
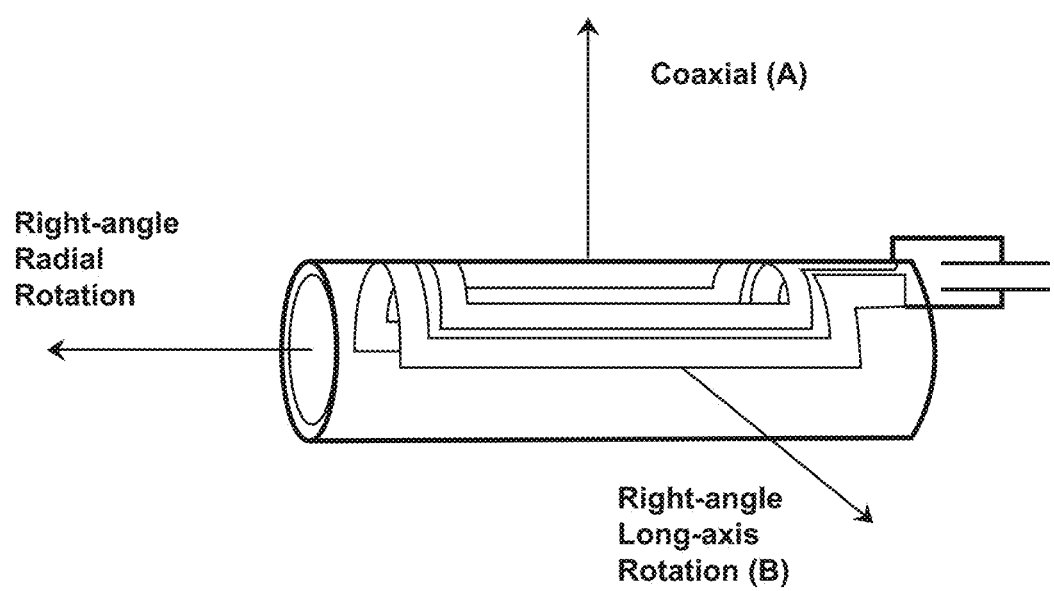
FIG. 15A illustrates an embodiment of orientations of an ingestible RFID tag with rectangular conductive elements in a tubular configuration relative to an RFID reader.
Figure 15B:
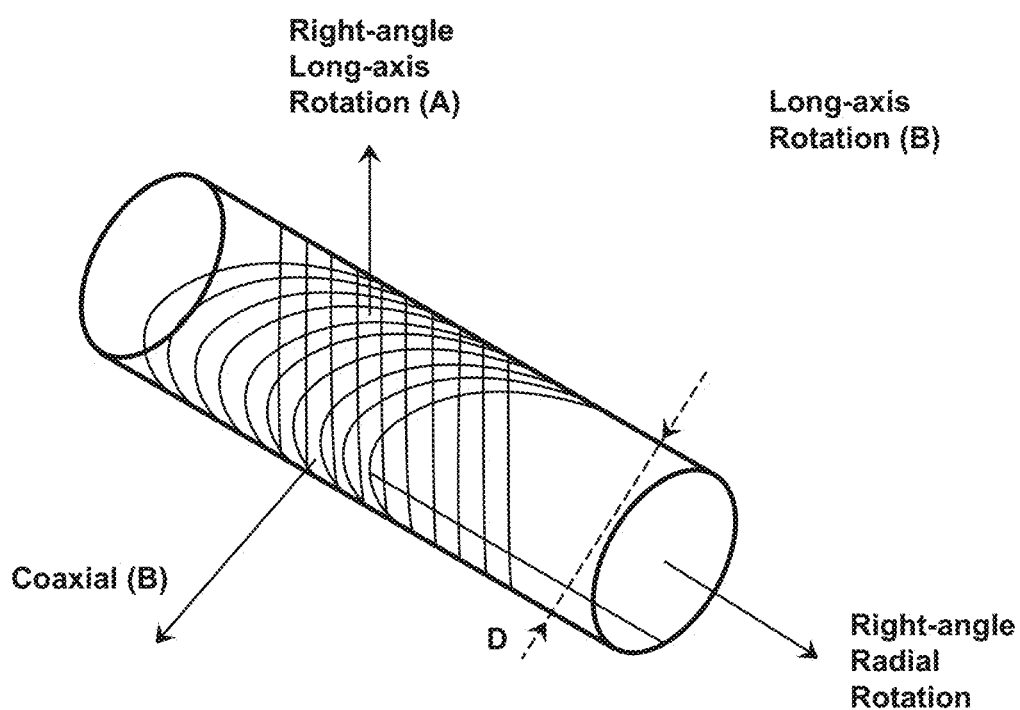
FIG. 15B illustrates an embodiment of orientations of an ingestible RFID tag with sinusoidal conductive elements in a tubular configuration relative to an RFID reader.

The RFID tag 102 in FIG. 8A is shown with the conductive elements 110 having a plurality of turns to form the rectangular coil pattern, where the conductive elements are shown with eight turns, however the RFID tag 102 can include different numbers of turns. For example, the plurality of turns can be from five turns to twenty-five turns to accommodate different sizes of the capsule 200 (e.g., size 00 capsules, size 000 capsules, etc.). The width of the conductive element 110 used to make the coil can affect the number of turns available for a given RFID tag 102, dependent on the size of capsule 200 into which the RFID tag 102 is to be introduced. For example, a wider conductive element 110 can be used for fewer turns as compared to a narrower conductive element 110 for the same area of the flexible substrate 104. In some embodiments, the spacing between turns of the conductive elements is approximately three-thousands of an inch spacing between turns. In embodiments, the flexible substrate 104 is sized and dimensioned to fit within the capsule 200 in the tubular configuration (e.g., as shown in FIGS. 2 and 15A), but not in the planar configuration (e.g., shown in FIG. 8A). For example, the flexible substrate 104 can have a length from about 20 mm to about 30 mm and can have a width from about 15 mm to about 20 mm. In an embodiment, the flexible substrate 104 has a length of about 24 mm and a width of about 16 mm to accommodate insertion into a 00 size capsule in the tubular configuration. In an embodiment, the flexible substrate 104 has a length of about 28 mm and a width of about 18 mm to accommodate insertion into a 000 size capsule in the tubular configuration.

The conductive elements 110 can include multiple coil configurations on the first side 112 of the flexible substrate 104. For example, the example RFID tag 102 of FIG. 8A includes a first coil configuration 802 on the first side 112 of the flexible substrate 104 and a second coil configuration 804 opposing the first coil configuration 802 on the first side 112 of the flexible substrate. In some embodiments, the first coil configuration 802 includes the same pattern, number of turns, or combinations thereof, as the second coil configuration 804. For example, in FIG. 8A, the first coil configuration 802 and the second coil configuration 804 each includes eight turns of the conductive elements 110 arranged in a substantially rectangular pattern.

In some embodiments, the RFID tag 102 includes the conductive elements 110 arranged on each of the first side 112 of the flexible substrate 104 and the second side 506 of the flexible substrate 104. For example, FIG. 8A shows a top view of the RFID tag 102 with the conductive elements 110 disposed on the first side 112 of the flexible substrate 104, whereas FIG. 8B shows a bottom view of the RFID tag 102 with the conductive elements 110 disposed on the second side 506 of the flexible substrate 104. Throughholes or vias can electrically connect conductive elements 110 on the first side 112 to conductive elements 110 on the second side 506. For example, FIG. 8A shows a first group of vias 806 formed with conductive elements 110 within the interior region 800 formed by the first coil configuration 802 and a second group of vias 808 formed with conductive elements 110 within the interior region 800 formed by the second coil configuration 804. In embodiments, shown in FIG. 8B, the vias 806 are electrically connected with the vias 808 by a conductive element 810 that traverses the second side 506 of the flexible substrate (e.g., for a distance between interior regions 800 formed on the first side 112 of the flexible substrate 104). The conductive elements 110 can further define connections for one or more tuning capacitors to tune the RFID tag 102. For example, FIG. 8A shows a first tuning capacitor pad 810 coupled to the flexible substrate 104 within the interior region 800 formed by the first coil configuration 802 on the first side 112, and FIG. 8B shows a second tuning capacitor pad 812 coupled to the flexible substrate 104 on the second side 506.

Figure 9:
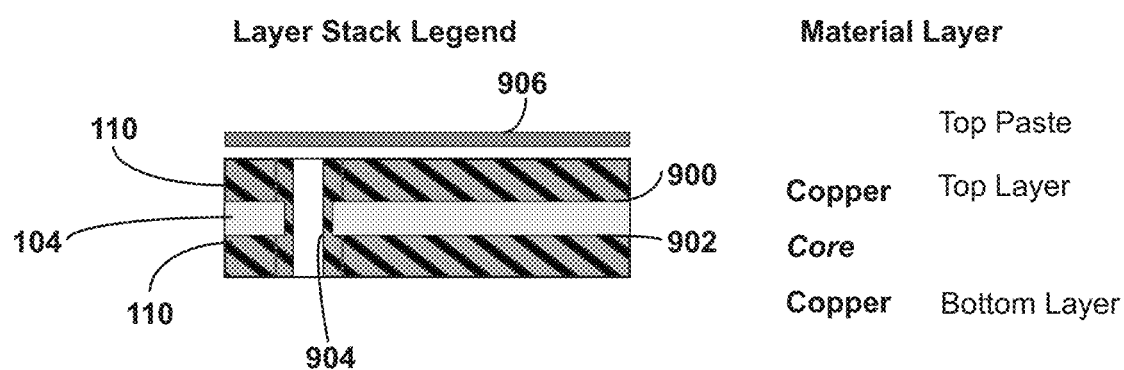
FIG. 9 illustrates a partial cross-sectional view of an ingestible RFID tag in a planar configuration.

Referring to FIG. 9, a cross-section of an example ingestible RFID tag 102 in a planar configuration is shown. The RFID tag 102 includes the deformable substrate 104 having conductive elements 110 on opposing sides of the deformable substrate 104. The conductive elements 110 include a top layer disposed on a first side 900 of the deformable substrate 104, which can correspond to the first side 112, the first side 116, the first side 502, for example. The conductive elements also include a bottom layer disposed on a second side 902 of the deformable substrate 104, which can correspond to the second side 506 or a side of the deformable substrate 104 opposing the first side 112, the first side 116, or the like. The RFID tag 102 also includes a via (e.g., via 904) through the deformable substrate 104, the top layer, and the bottom layer, to electrically connect the conductive elements 110 of the top layer and the bottom layer (e.g., disposed on the first side 112 and the second side 506). For example, the via 904 can represent vias 806 or 808 described with respect to FIGS. 8A and 8B. In the example shown in FIG. 9, the deformable substrate 104 is composed of a dielectric material (e.g., polyimide) having a thickness of about 0.025 mm and the conductive elements 110 of the top layer and bottom layer are composed of a conductive material (e.g., copper, aluminum, gold, silver, alloys thereof, etc.) and can have a thickness of about 0.036 mm. The dimensions of the components can depend on the size of the capsule 200 into which the RFID tag is to be positioned. The RFID tag 102 can also include a binder 906 (e.g., a paste, such as solder paste) to mount the RFID tag chip 114 to the conductive elements 110 while permitting electrical conductivity therethrough.

The system 100 and associated RFID tags 102 described herein can facilitate verification that a medication has been ingested by a patient, such as within a recent time period. For example, treatment of tuberculosis or other infectious diseases can involve multiple doses of antibiotics or other medications taken periodically (e.g., daily, weekly, etc.) over the course of multiple weeks or months. A treatment facility, healthcare staff, or other healthcare provider may monitor compliance of a medication course by tracking whether a patient ingests the medication at the treatment facility and during which period(s) of time. However, a patient may feign ingestion or other spoof the ingestion of the medication to avoid actual or prolonged ingestion. For example, the patient may hold the medication in clothing or on their person rather than swallow the medication. For instance, if location sensors are used to track individual doses of the medication, the presence of the medication in clothing or on their person may obfuscate the actual status of the medication (e.g., ingested or merely held close to the stomach). Alternatively or additionally, the patient may hold the medication in their oral cavity, esophagus, larynx, or other location to feign ingesting the medication without swallowing the medication to the stomach. In embodiments, the system 100 can include a structure (e.g., a pH switch structure) associated with the capsule 200 to interfere with communication between the RFID tag 102 and the RFID reader 105 in a first configuration and to permit or otherwise cease to interfere with communication between the RFID tag 102 and the RFID reader 105 in a second configuration that can facilitate detection of the capsule 200 in the stomach of the patient without detection of the capsule 200 outside the patient's stomach.

Figure 12:
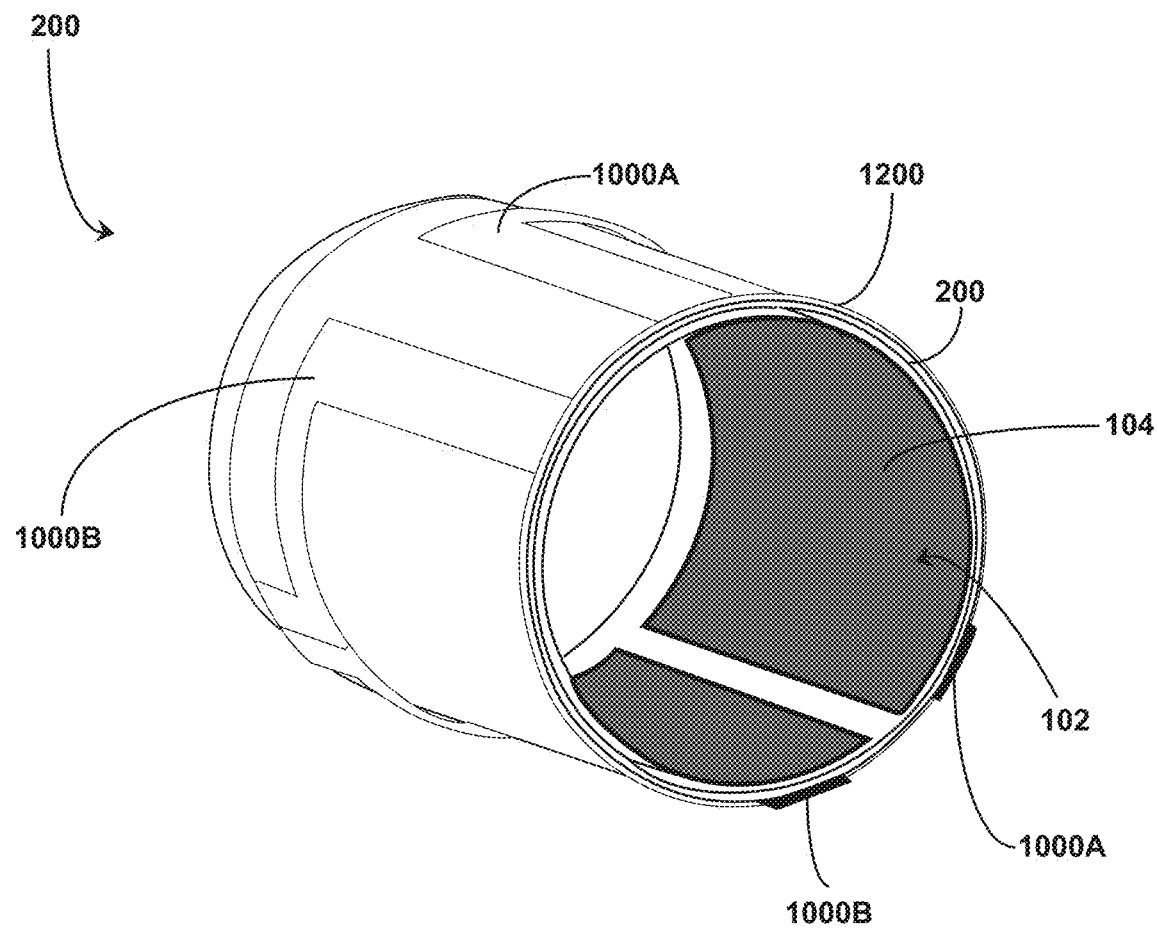
FIG. 12 illustrates an isometric view of an end of an ingestible RFID tag in a tubular configuration positioned within a capsule having a pH active structure.

For example, the first configuration can be maintained while the RFID tag 102 and corresponding medication is located in an environment outside of the patient (e.g., in the patient's clothes, in the healthcare facility, in storage, etc.) or outside of the stomach of the patient (e.g., in the mouth, oral cavity, esophagus, larynx, or other location) to prevent communication between the RFID tag 102 and the RFID reader 105 while the medication is outside the stomach of the individual. The structure can adopt the second configuration while in the stomach, where communication between the RFID tag 102 and the RFID reader 105 is permitted to ensure that the RFID tag 102 and associated medication is within the stomach of the patient. For example, the RFID tag 102 can be positioned within the interior of the capsule 200 (e.g., folded into the tubular state, as shown in FIGS. 2, 6F, 12), where the capsule 200 is fitted with a pH switch structure that utilizes a pH trigger to modify the configuration of the structure. For instance, the pH trigger can be a change in an environment of the capsule 200 to change the pH switch structure from the first configuration to the second configuration upon exposure to a pH associated with the stomach (e.g., having a pH of about 5.0 or less than 5.0), but not associated with another body portion (e.g., oral cavity having a pH from about 6.2 to about 7.3). In embodiments, the pH switch structure is formed from a biocompatible metal that can be dissolved by stomach acids to transition the structure from the first configuration, where the presence of the pH switch structure shields or otherwise prevents electromagnetic communication, to the second configuration where the absence of the pH switch structure or portions thereof permits electromagnetic communication between the RFID tag 102 and the RFID reader 105. The pH switch structure can therefore remain intact outside the patient's body to prevent activation of the RFID tag 102 and can dissolve upon exposure to the stomach environment.

In embodiments, the system 100 utilizes materials to influence the time at which the RFID tag 102 is traceable by the RFID reader 105 following ingestion and/or the duration that the RFID tag 102 is traceable within the stomach of the patient by the RFID reader 105. For example, the structure used to influence communications between the RFID tag 102 and the RFID reader 105 can maintain structural integrity within the stomach for a certain duration (e.g., maintaining the first configuration) to prevent communications until a sufficient duration within the stomach has passed (e.g., from about 1 minute to about 10 minutes). Alternatively or additionally, one or more components of the RFID tag 102 can maintain structural integrity within the stomach to permit operation of the RFID tag 102 during interrogation by the RFID reader 105 for a duration corresponding with a next dose of the medication (e.g., from about 30 minutes to about six hours) before structural failure of the RFID tag 102 within the digestive system of the patient. Such stability of the RFID tag 102 can ensure that if the RFID tag 102 is identified by the RFID reader 105, the identification is associated with medication taken by the patient during that dosing period (e.g., that day) as opposed to medication taken during a prior dose that is still within the patient's digestive system, since such prior dose will no longer have a functional RFID tag 102.

For an example medication compliance regime, a patient is initially scanned with the RFID reader 105 to ensure no medication associated with the healthcare facility is currently in the patient's stomach. The patient is then given the capsule 200 containing the medication and the RFID tag 102. The capsule 200 includes the pH switch structure to influence communications between the RFID tag 102 and the RFID reader 105 as described herein. The patient swallows the capsule 200 and for a period of time (e.g., from ingestion to a period of up to about 10 minutes), the RFID reader 105 is unable to record the presence of the RFID tag 102 within the patient (e.g., the pH switch structure is still in the first configuration, since the current duration of exposure to stomach acid is insufficient to transition the structure to the second configuration or state of dissolution). Once the capsule 200 is within the stomach for a sufficient duration (e.g., from about 1 minute to about 10 minutes), the stomach acid is exposed to the pH switch structure for enough time to sufficiently dissolve the pH switch structure to transition the structure to the second configuration. The second configuration can include total or partial dissolution of the pH switch structure into the stomach acid, where the structure no longer impedes the communication between the RFID tag 102 and the RFID reader 105, thereby permitting recognition of the RFID tag 102 within the patient. The following day, the patient is again scanned with the RFID reader 105 to ensure that the prior day's RFID tag 102 is no longer operational. For instance, the materials of the RFID tag 102 has degraded within the digestive system of the patient to the extent that the RFID tag 102 does not sufficiently respond to interrogation by the RFID reader 105. The patient is given the next dose of medication, where following the initial delay period, the RFID reader 105 confirms the presence of the current dose of medication. Alternatively, the patient is scanned once during each visit—after the delay period following ingestion of the medication, since the RFID tag 102 of the current dose is unable to communicate with the RFID reader 105 until after the delay period, and any RFID tags 102 of previous doses would be rendered sufficiently inoperable due to length of time in the patient's digestive tract.

Examples of the structure associated with the capsule 200 to interfere with communication between the RFID tag 102 and the RFID reader 105 are provided below. While examples used herein focus on tracking ingestion by altering communications between the RFID tag 102 and the RFID reader 105 via conditions in the stomach, the system 100 is not limited to such alterations occurring in the stomach. For example, other environmental conditions (e.g., different pH environments, specific chemical triggers, specific enzymatic or other biological component triggers, etc.) can be used to trigger alteration of the communications between the RFID tag 102 and the RFID reader 105.

Figure 10:
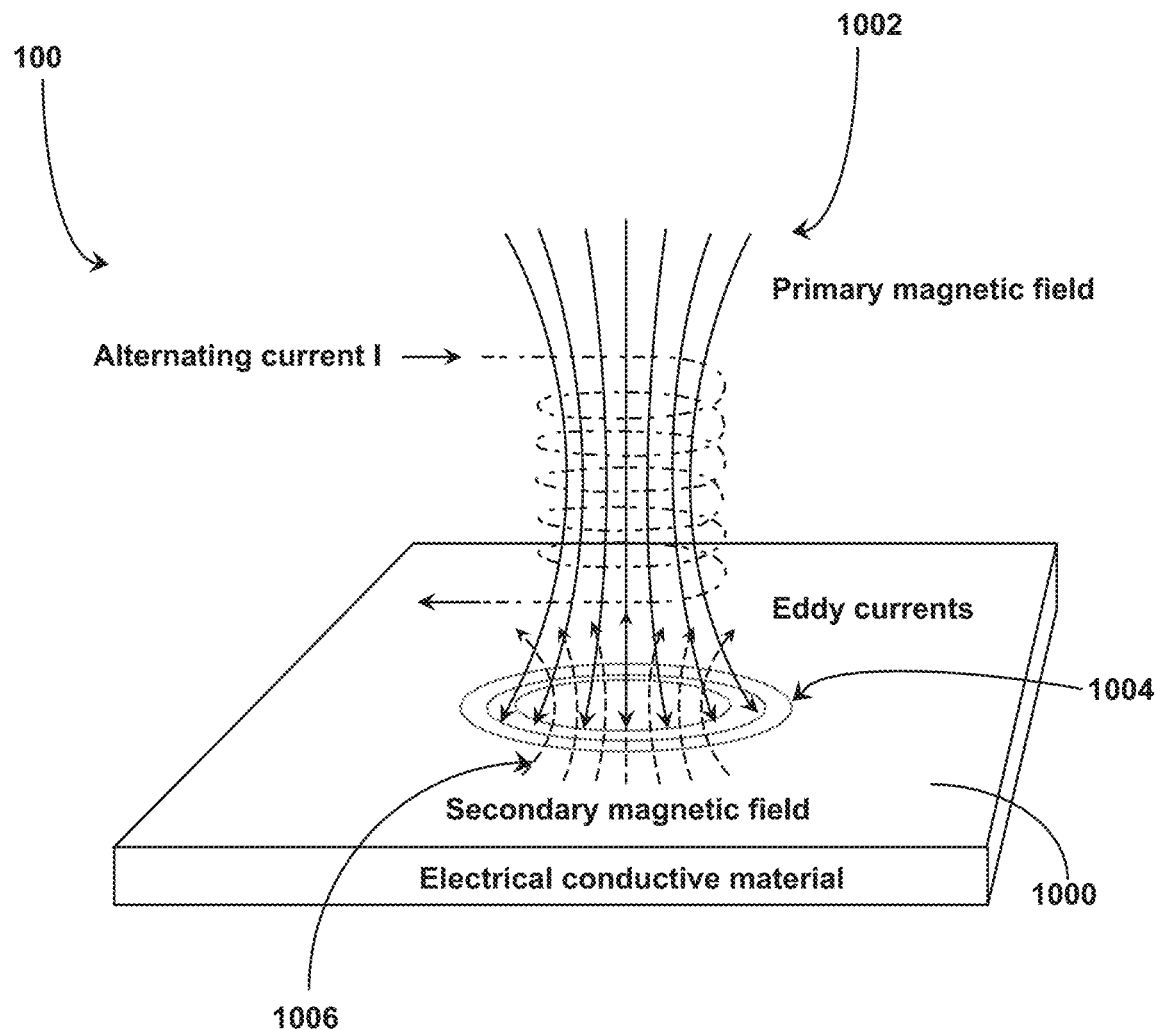
FIG. 10 is a diagrammatic view of an electromagnetic shield provided by a capsule surface feature.

Referring to FIG. 10, the system 100 can include a structure 1000 (e.g., a pH switch structure) formed from an electrically conductive material to be placed around at least a portion of the capsule 200 to interfere with communication between the RFID tag 102 and the RFID reader 105. The electrically conductive material may or may not be ferromagnetic. In operation, when the structure 1000 is exposed to an alternating magnetic field 1002 (e.g., via the RFID reader 105), the structure 1000 facilitates the generation of eddy currents 1004 which in turn generate magnetic fields 1006 opposing the alternating magnetic field 1002. The magnetic fields 1006 can disrupt the interrogation signals from the RFID reader 105 and/or otherwise disable the functionality of the RFID tag 102 within the capsule 200 (e.g., via insufficient energy reaching the RFID tag 102 for power). For example, with high frequency magnetic fields 1002, a thin layer of structure 1000 around an external surface of the capsule 200 can disable functionality of the RFID tag 102 within the capsule 200. In embodiments, the structure 1000 coats at least a portion the external surface of the capsule 200 to provide shielding of the communications between the RFID tag 102 and the RFID reader 105. In embodiments, the structure 1000 coats the whole external surface of the capsule 200 to provide shielding of the communications between the RFID tag 102 and the RFID reader 105. The structure 1000 can be applied to the capsule 200 utilizing a plating technique, including but not limited to, dip coating, chemical vapor deposition (CVD), physical vapor deposition (PVD), or combinations thereof. In embodiments, the structure 1000 is applied directly to the external surface of the capsule 200. In embodiments, an intervening layer is introduced between the capsule 200 and the structure 1000. For example, the capsule 200 can include an intervening layer on the external surface and the structure 1000 is applied to the intervening layer utilizing a plating technique, including but not limited to, dip coating, chemical vapor deposition (CVD), physical vapor deposition (PVD), or combinations thereof. The intervening layer can include, but is not limited to, an acid-soluble substrate. In embodiments, the intervening layer includes an acid-soluble substrate that is dissolvable in an acidic environment having a pH at or below 5.0 and is not substantially dissolvable at a pH above 6.0. For example, the acid-soluble substrate can include, but is not limited to, EUDRAGIT™ E PO polymer available from Evonik (Essen, Germany). The acid-soluble substrate can dissolve when exposed to the acidic environment of the stomach to remove the structure 1000 from the external surface of the capsule 200, thereby permitting activation of the RFID tag 102 within the capsule 200 when interrogated by the RFID reader 105.

Figure 11:
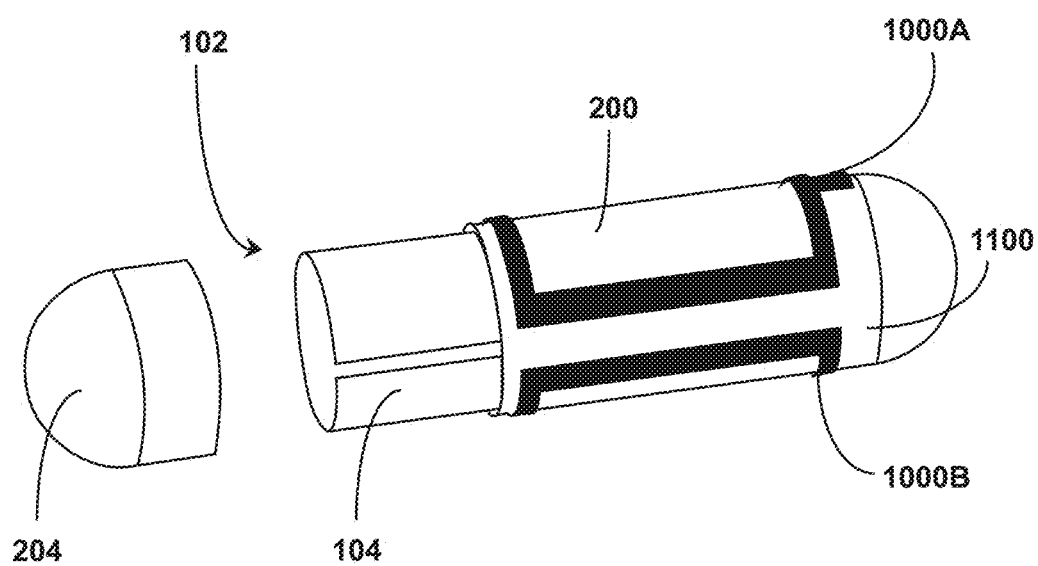
FIG. 11 illustrates an isometric view of an ingestible RFID tag in a tubular configuration positioned within a capsule having an energy absorption structure.

In embodiments, the electrically conductive material that forms the structure 1000 is dissolvable upon exposure to chemical located in a target area for the medication (e.g., dissolvable in stomach acid for medication ingested orally). The structure 1000 can be formed from a biocompatible metal that reacts with hydrochloric acid in the stomach. For example, the structure 1000 can be formed from magnesium, zinc, iron, alloys thereof, or combinations thereof. The structure 1000 is maintained in the first configuration to prevent communications between the RFID tag 102 and the RFID reader 105, rendering the RFID tag 102 deactivated while the structure 1000 is intact. Upon exposure of the structure 1000 to chemical located in the target area (e.g., stomach acid), the structure 1000 dissolves to transition the structure 1000 to the second configuration. In the second configuration, the structure 1000 permits activation of the RFID tag 102 upon interrogation by the RFID reader 105, for example, due to the inability to generate the eddy currents 1004 or sufficient opposing magnetic fields 1006. In embodiments, the structure 1000 is formed as one or more shorted turn structures on the exterior surface of the capsule 200 to absorb energy transmitted between the RFID reader 105 to the RFID tag 102. For example, referring to FIGS. 11 and 12, the structure 1000 is formed as a pair of shorted turn structures (1000A and 10008 are shown) coupled to an exterior surface 1100 of the capsule 200. The shorted turn structures 1000 are coupled to a portion of the exterior surface 1100 as opposed to covering the whole exterior surface 1100. The shorted turn structures 1000 are conductors each formed as a continuous circuit that disrupt the functioning of the interaction between the RFID tag 102 and the RFID reader 105. For instance, a reader coil of the RFID reader 105 and a corresponding tag coil of the RFID tag 102 (e.g., the rectangular coils shown in FIG. 8A) can function as a magnetic transformer. The shorted turn structures 1000 can absorb energy transmitted from the RFID reader 105 before being received by the RFID tag 102 in an amount sufficient to render the RFID tag 102 nonfunctional due to insufficient energy for power.

If the shorted turn structures 1000 no longer maintain the continuous circuit structure, the shorted turn structures 1000 can no longer form short circuits for the energy transferred from the RFID reader 105, thereby permitting functioning of the RFID tag 102. The shorted turn structures 1000 can therefore operate as a pH switch structure by removing all or portions of the structure 1000 upon exposure to a pH-specific environment, such as the stomach of the patient. For example, in embodiments, one or more shorted turn structures 1000 are applied directly to the exterior surface 1100 of the capsule 200 utilizing a plating technique, including but not limited to, dip coating, chemical vapor deposition (CVD), physical vapor deposition (PVD), or combinations thereof. In some embodiments, capsule 200 can include an intervening layer on the external surface 1100 with the shorted turn structure 1000 applied to the intervening layer utilizing a plating technique, including but not limited to, dip coating, chemical vapor deposition (CVD), physical vapor deposition (PVD), or combinations thereof. FIG. 12 illustrates shorted turn structures 1000A and 1000B coupled to intervening layer 1200 which in turn is coupled to the exterior surface 1100 of the capsule 200. The intervening layer 1200 can include, but is not limited to, an acid-soluble substrate. In embodiments, the intervening layer 1200 includes an acid-soluble substrate that is dissolvable in an acidic environment having a pH at or below 5.0 and is not substantially dissolvable at a pH above 6.0. For example, the acid-soluble substrate can include, but is not limited to, EUDRAGIT™ E PO polymer available from Evonik (Essen, Germany). The acid-soluble substrate can dissolve when exposed to the acidic environment of the stomach to remove the shorted turn structure 1000 from the external surface 1100 of the capsule 200, thereby permitting activation of the RFID tag 102 within the capsule 200 when interrogated by the RFID reader 105.

The shorted turn structure 1000 can be formed from a single conductive material or multiple conductive materials to provide energy absorption functionality. For single material shorted turn structures 1000, a portion of the shorted turn structure can have a material thickness (e.g., normal to the external surface 1100) that is thinner than the other portions of the shorted turn structure. The thinner portion can fully dissolve to break the continuous circuit structure when exposed to the acidic environment of the patient before the other portions of the shorted turn structure 1000 due to less material needing to dissolve before the continuous circuit structure is broken. For example, the thinner portion can act as an acid-reactive fuse to disable the shorted turn structure 1000 upon reacting with stomach acid. The thicker portions of the shorted turn structure 1000 can keep resistance of the shorted turn structure 1000 low to provide improved shielding effectiveness as compared to a shorted turn structure 1000 with the whole continuous circuit structure having thickness of the thinner portion. Similarly, for shorted turn structures 1000 formed from multiple materials, a portion of the shorted turn structure can have a material thickness (e.g., normal to the external surface 1100) that is thinner and formed from a first material with the other portions of the shorted turn structure having greater material thickness formed from one or more different electrically conductive materials. In embodiments, the thinner portion of the shorted turn structure 1000 is formed from a first electrically conductive material and the thicker portion of the shorted turn structure 1000 is formed from a second electrically conductive material. In embodiments, the first electrically conductive material includes at least one of magnesium, zinc, or iron, or an alloy thereof and the second electrically conductive material includes at least one of gold, silver, or copper, or an alloy thereof. The first electrically conductive material can be a material having a higher reactivity with stomach acid to cause failure of the shorted turn structure 1000 at the thinner portion as compared to the material reactivity with stomach acid of the second electrically conductive material.

Example Ex Vivo Experiments

Figure 13:
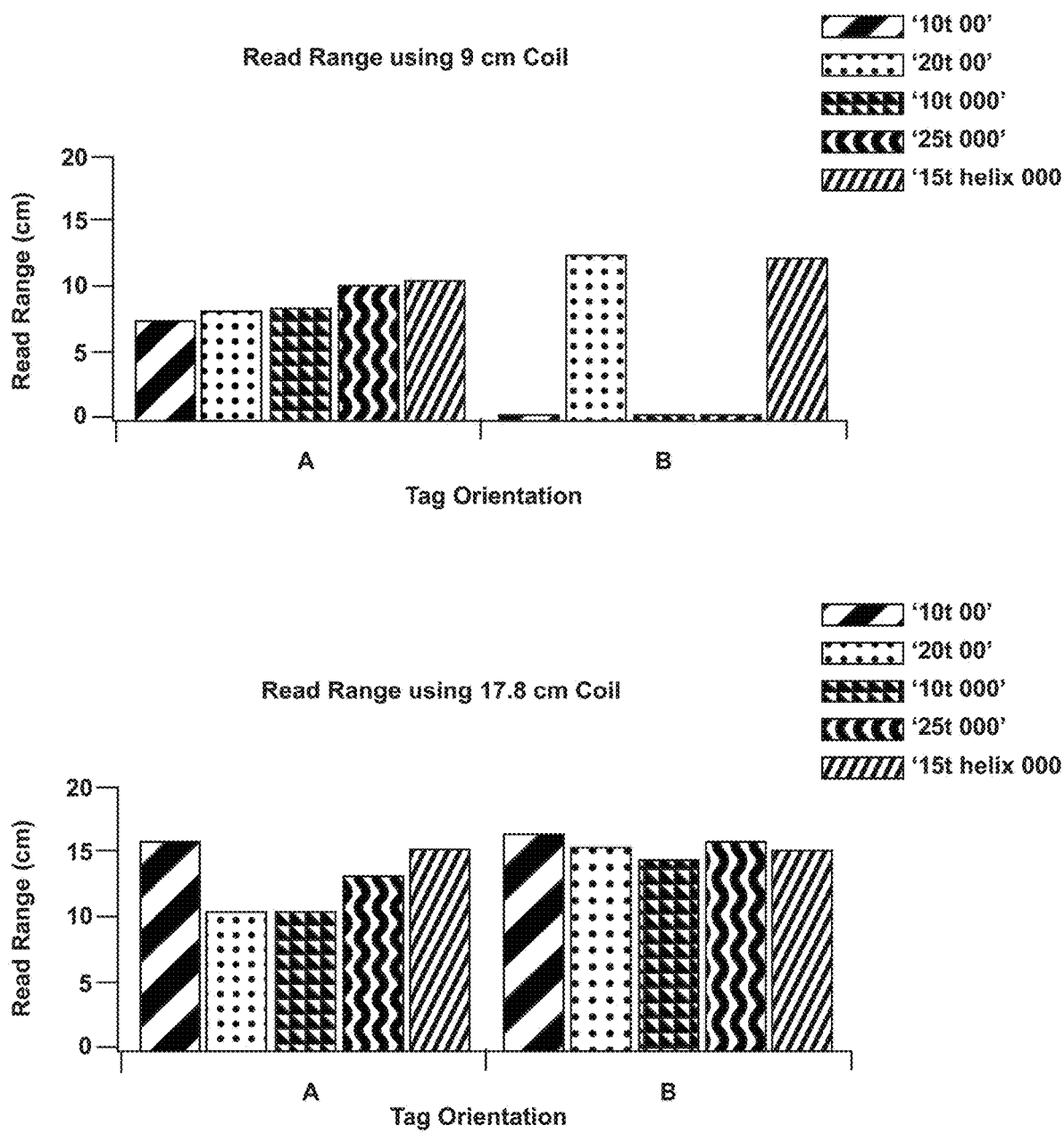
FIG. 13 is a chart of read range measurements for different orientations of an embodiment of an RFID reader relative to an ex vivo ingestible RFID tag.

Experiments were performed to determine the read range of various RFID tag configurations (having the RFID chip hardware located on the tab segment 124, such as shown in FIGS. 4-6E) placed internally in cadaver animals utilizing two different RFID reader configurations. Example results are shown in FIG. 13. For each test, the RFID tag (e.g., RFID tag 102) was positioned into the folded or tubular configuration (e.g., as shown in FIG. 2) and placed inside a capsule (of a 00 or a 000 size). The capsule was placed inside a PVC cylinder (1.6 cm diameter, with 3.8 cm between an end of the cylinder and an end of the capsule) for implantation into a swine belly. Five different RFID tag configurations were utilized: a ten turn coil configuration for a 00 capsule (e.g., shown in FIG. 6B in a planar configuration), a twenty turn coil configuration for a 00 capsule (e.g., shown in FIG. 6D in a planar configuration), a ten turn coil configuration for a 000 capsule (e.g., shown in FIG. 4 in a planar configuration), a twenty-five turn coil configuration for a 000 capsule (e.g., shown in FIG. 6A in a planar configuration), and a fifteen turn helix or sinusoidal coil for a 000 capsule (e.g., shown in FIG. 5 in a planar configuration). The tags were selected for the ex vivo experiment on the basis of data generated during bench experiments (data shown with respect to FIG. 9). Two different RFID readers were utilized: a 9 cm wide coil (e.g., shown in FIG. 3) and a 17.8 cm wide coil. Each RFID tag was interrogated by each RFID reader from two different orientations: orientation A and orientation B, where the respective orientation for the RFID tags is shown with respect to FIG. 10A (for the planar-coil tags (e.g., ten turn for 00 capsule, twenty turn for 00 capsule, ten turn for 000 capsule, and twenty-five turn for 000 capsule)) and 10B (for the helix or sinusoidal coil (e.g., fifteen turn helix for 000 capsule)). The read range for tag orientation B for the ten turn for 00 capsule, the ten turn for 000 capsule, and the twenty-five turn for 000 capsule tag configurations is displayed as zero, where the thickness of the swine belly may have been wider than the minimum read range for each of the tag configurations. Bench experiments provide additional read range measurements for the example RFID tags in air and saline environments, with example data shown in FIG. 14 described further herein.

Example In Vivo Experiments

Experiments were performed to determine the read range of various RFID tag configurations (having the general configuration of FIGS. 8A and 8B) placed internally in sedated animals utilizing different RFID reader configurations. A pig model was used for the testing, where the pig was sedated during the testing. A small diameter tube was placed down the esophagus to facilitate placement of capsules containing RFID tags in the tubular configuration inside the stomach of the pig. The capsule was carefully introduced down the tube until it entered the stomach. A fluoroscope was used to verify the location of the capsule in the stomach. The fluoroscope was also used to determine the physical distance from the outside skin to the RFID tag. Two distances were measured: (1) from the back of the pig to the RFID tag; and (2) from the side of the pig to the RFID tag). Reader-antenna performance (e.g., ability and/or capability to detect the RFID tags) was measured at both back and side positions, which are generally aligned along orientations A and B shown in FIG. 15A (e.g., short axis orientations).

Several RFID reader configurations were tested, with different reader models and antenna sizes evaluated. The RFID reader assemblies included a commercial reader module (Andea M20 Reader Assembly with 1.5 W power rating; Andea M202 Reader Assembly with 1.5 W power rating) with a battery power subsystem housed inside an off-the-shelf enclosure. The reader assemblies incorporated a standard connector that permitted switching between the different antenna sizes that were evaluated. Four antenna sizes were used during the in vivo testing: 90 mm re-tuned antenna, 116 mm antenna, 130 mm antenna, 170 mm antenna.

Two capsule-tag configurations were used during testing: (1) an RFID tag having the configuration of FIGS. 8A and 8B placed in the tubular configuration within a 000 size capsule coated in epoxy; and (2) an RFID tag having the configuration of FIGS. 8A and 8B placed in the tubular configuration within a 00 size capsule, which in turn is placed within a 000 size capsule coated in epoxy.

In a first test, a capsule with the first capsule-tag configuration was introduced to the stomach. Fluoroscope evaluation indicated that the capsule was located in stomach, and that the internal distance from tag to skin (side direction) was approximately 12 cm. Results of the initial analyses are shown in Table 1.

TABLE 1

| | Side Position | Back Position |
| --- | --- | --- |
| M20 with 90 mm retuned antenna | ~1.5 cm from skin | ~2.0 cm from skin |
| M20 with 130 mm antenna | ~5.0 cm from skin | |
| M20 with 170 mm antenna | ~10.0 cm from skin | ~6.0 cm from skin |
| M202 with 90 mm retuned antenna | ~1.5 cm from skin | ~2.0 cm from skin |
| M202 with 116 mm antenna | ~5.25 cm from skin | |

Observations were made that the capsule appeared to be slightly rotating within the stomach, so several readings were reanalyzed. As an example, the M20 reader with a 90 mm retuned antenna detected the tag from the side position at approximately 3.0 cm from the skin and from the back position at the skin surface.

The capsule positioning was reevaluated with the fluoroscope, which indicated that the capsule was located in the stomach, but had slightly shifted in position, with the internal distance from the tag to skin in the side direction was approximately 12 cm and from the tag to skin in the back direction was approximately 16 cm. Results of analyses with this positioning is shown in Table 2.

TABLE 2

| | Side Position | Back Position |
| --- | --- | --- |
| M20 with 116 mm antenna | ~6.5 cm from skin | ~2.5 cm from skin |
| M20 with 130 mm antenna | ~6.5 cm from skin | ~3.0 cm from skin |
| M20 with 170 mm antenna | ~10 cm from skin | ~8 cm from skin |

In a second test, a capsule with the second capsule-tag configuration (00 capsule in 000 capsule) was introduced to the stomach. Fluoroscope evaluation indicated that the capsule was located in the stomach next to the capsule from the first test previously described. It was observed that when the tags from the capsules were next to each other, the communication field between tag and reader was disrupted resulting in lowered read range. Water (60 mL) was added to the stomach, which caused the capsules to move apart and perpendicular to one another. Read range improved as compared to when the capsules were positioned next to each other and returned to previous performance results. The tag within the capsule was detected from the side position for two reader configurations: M20 reader with 90 mm retuned antenna and M20 reader with 170 mm antenna.

In a third test, a capsule including the folded RFID tag having the configuration of FIGS. 8A and 8B was introduced to the stomach, where fluoroscope evaluation indicated that the capsule was located to another capsule in the stomach. An additional 60 mL of water was added to the stomach, which caused the capsules to move approximately 3 cm apart. The tag within the capsule was detected from the side position and from the back position for two reader configurations: M20 reader with 90 mm retuned antenna and M20 reader with 170 mm antenna. Tag detection was videoed and showed to be robust. The tag within the capsule was also detected from the side position at a range of approximately 5.0 cm from skin with an M20 reader with 116 mm antenna. An additional 60 mL of water to the stomach, which caused the capsules to move approximately 3 cm or greater apart. The tag within the capsule was then detected from the side position at a range of approximately 5.0 cm from skin with an M20 reader with 116 mm antenna and from the side position at a range of approximately 1.0 cm from skin with an M20 reader with 90 mm retuned antenna.

In a fourth test, a capsule including a tether and the folded RFID tag having the configuration of FIGS. 8A and 8B was introduced into the stomach via an esophagus tube. Fluoroscope evaluation indicated that the capsule slowly rotated on axis as the tether was twisted. The tag within the capsule was detected from the side position with an M20 reader with 90 mm retuned antenna, where it was observed that rotating the tag resulted in changing detection. The tag and the three other tags previously introduced to the stomach were detected from the side position at approximately 5.0 cm from skin.

Figure 16:
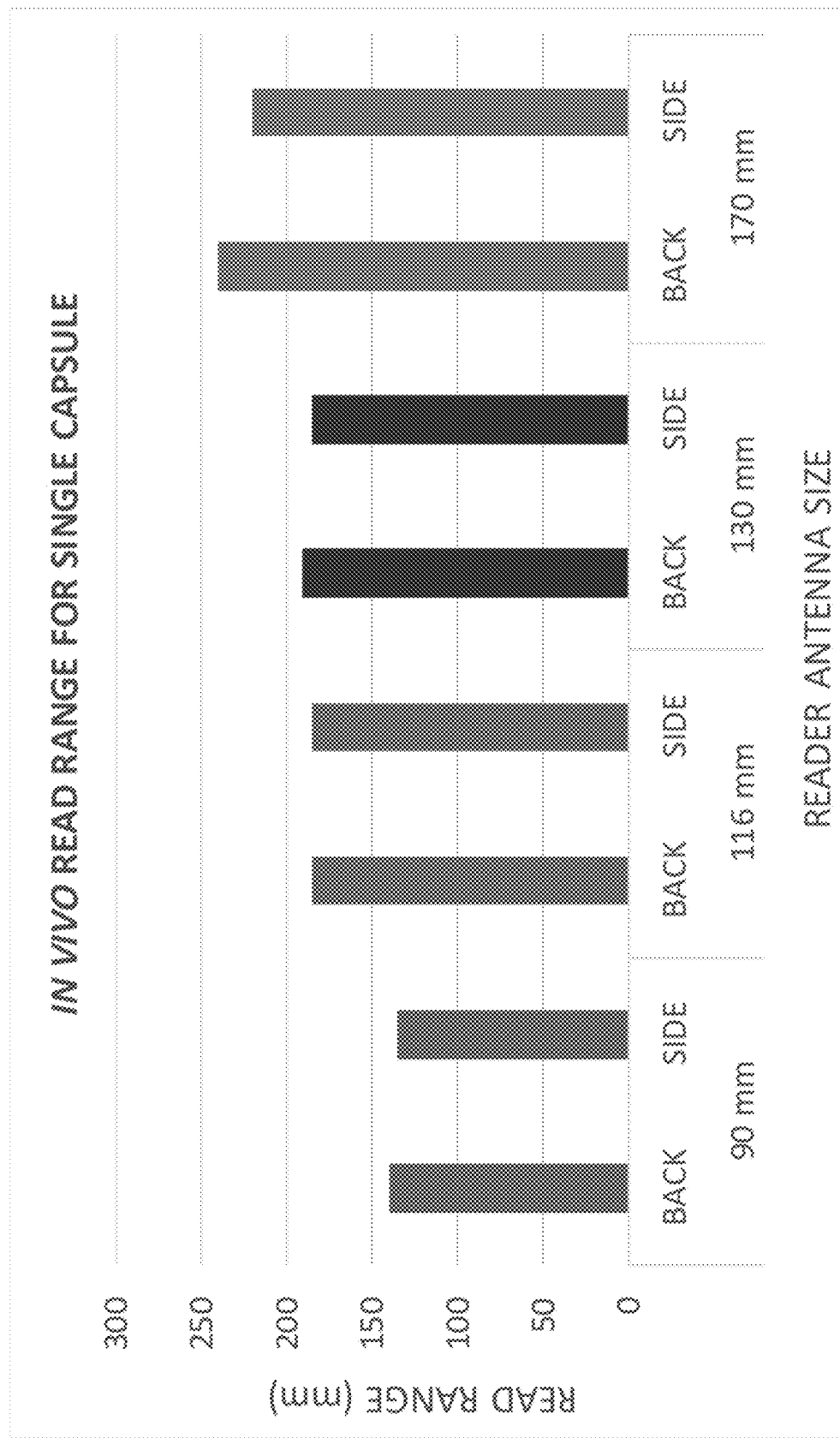
FIG. 16 is a chart of read range measurements for different orientations of an RFID reader relative to an in vivo ingestible RFID tag.

The in vivo tests resulted in successful detection of all tests tags for all reader-antenna combinations. Referring to FIG. 16, a chart showing read ranges from the back position and from the side position for various antenna sizes are shown for an example reader (M20). The read range data is similar to read range tests of the same RFID capsule during bench experiments in air with different combinations of reader types and antenna types, with example results shown in FIG. 17 (with antenna types on the y-axis (from bottom to top: 19.5 cm bespoke, 17 cm bespoke, DLP-RFID-ANT Original, DLP-RFID-ANT retuned, DLP-RFID-ANT, FEIG ISC.ANT100/100) and for each series the reader types from top to bottom are Andea M20, Andea M202, FEIG CPR74, FEIG MR102, and GAO-RFID 233006). The in vivo tests demonstrated that tag orientation impacts read range. The in vivo tests also suggested that tag proximity to another in vivo tag can reduce read range through interference.

Example Bench Experiments

Figure 14:
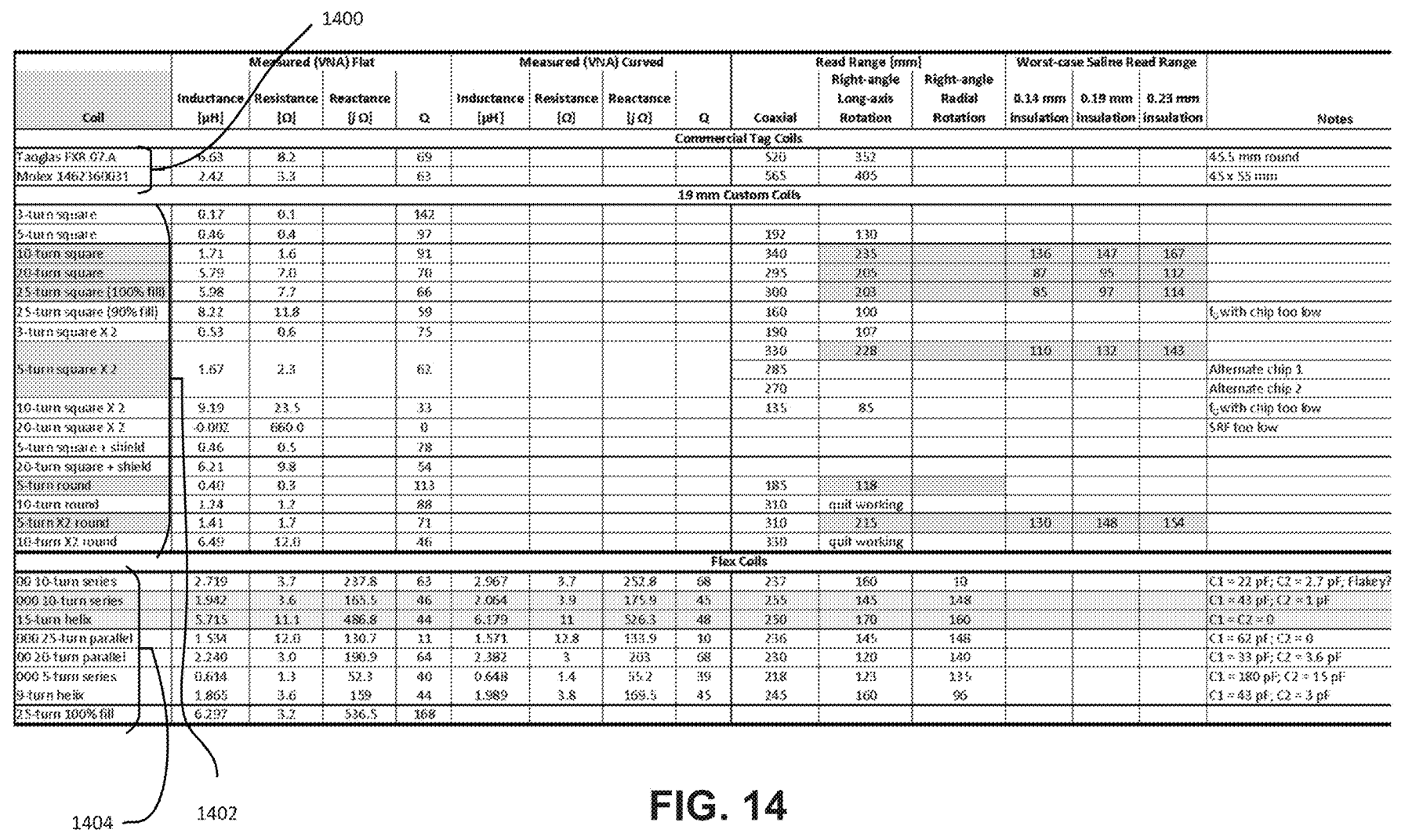

Experiments were performed to determine the read range of various RFID tag configurations in a planar configuration and with some of the RFID tags also in a folded or tubular configuration (e.g., as shown in FIG. 2). Example results are shown in FIG. 14, where rows labeled 1400 represent commercially available tags, rows labeled 1402 represent example RFID tags described herein, and rows labeled 1404 represent example RFID tags described herein tested in both planar configurations ("Measured (VNA) Flat") and folded or tubular configurations ("Measured (VNA) Curved"). The read range was measured according to one or more orientations of coaxial, right-angle long-axis rotation, or right-angle radial rotation. Examples of the orientations for RFID tags measured in the folded or tubular configurations are shown with respect to FIGS. 15A (for the planar-coil tags) and 15B (for the helix or sinusoidal tags).

Figure 19:
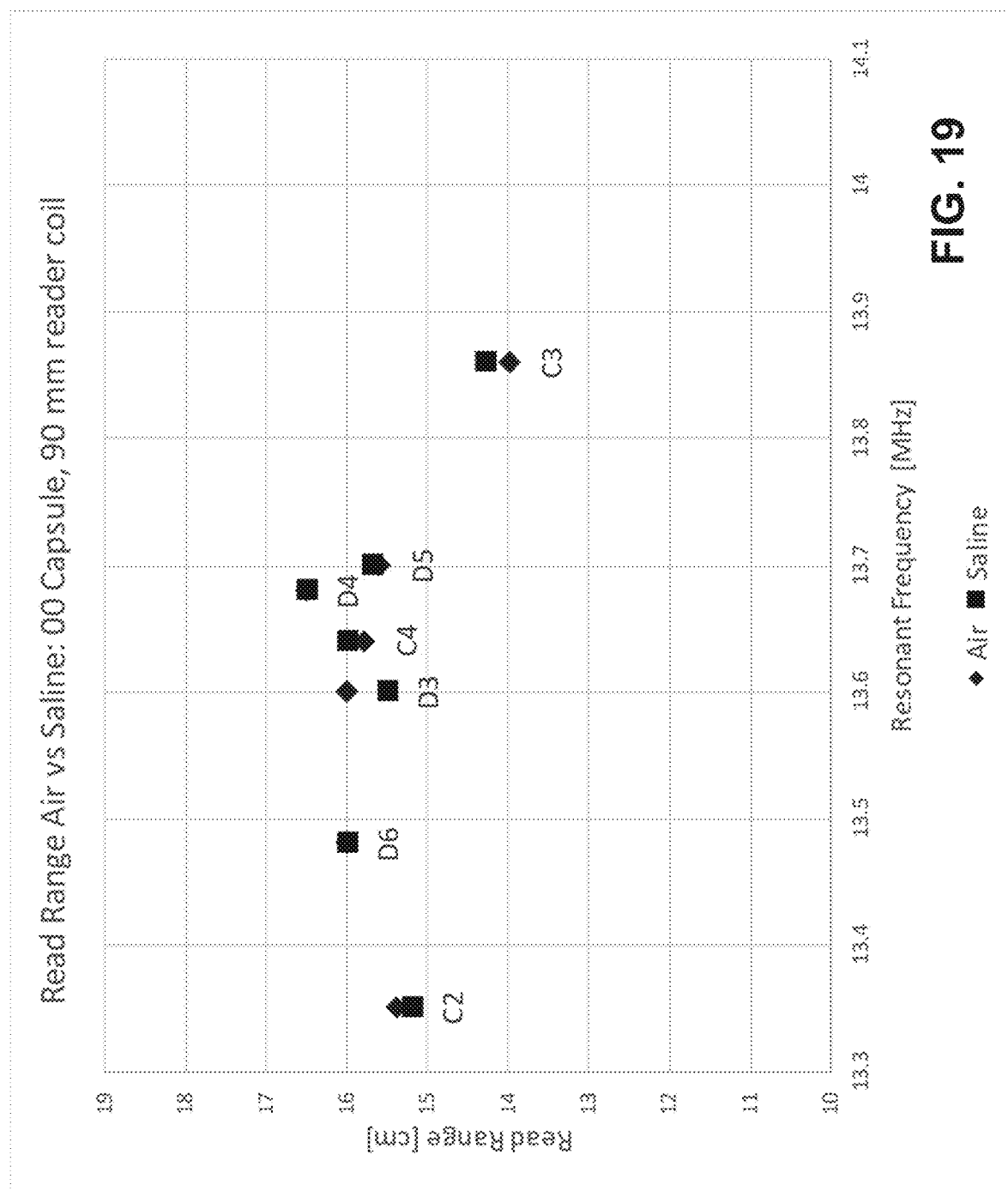
FIG. 19 is a chart of measured read ranges versus resonant frequency for 00 size capsules in air and in saline from example experiments.
Figure 20:
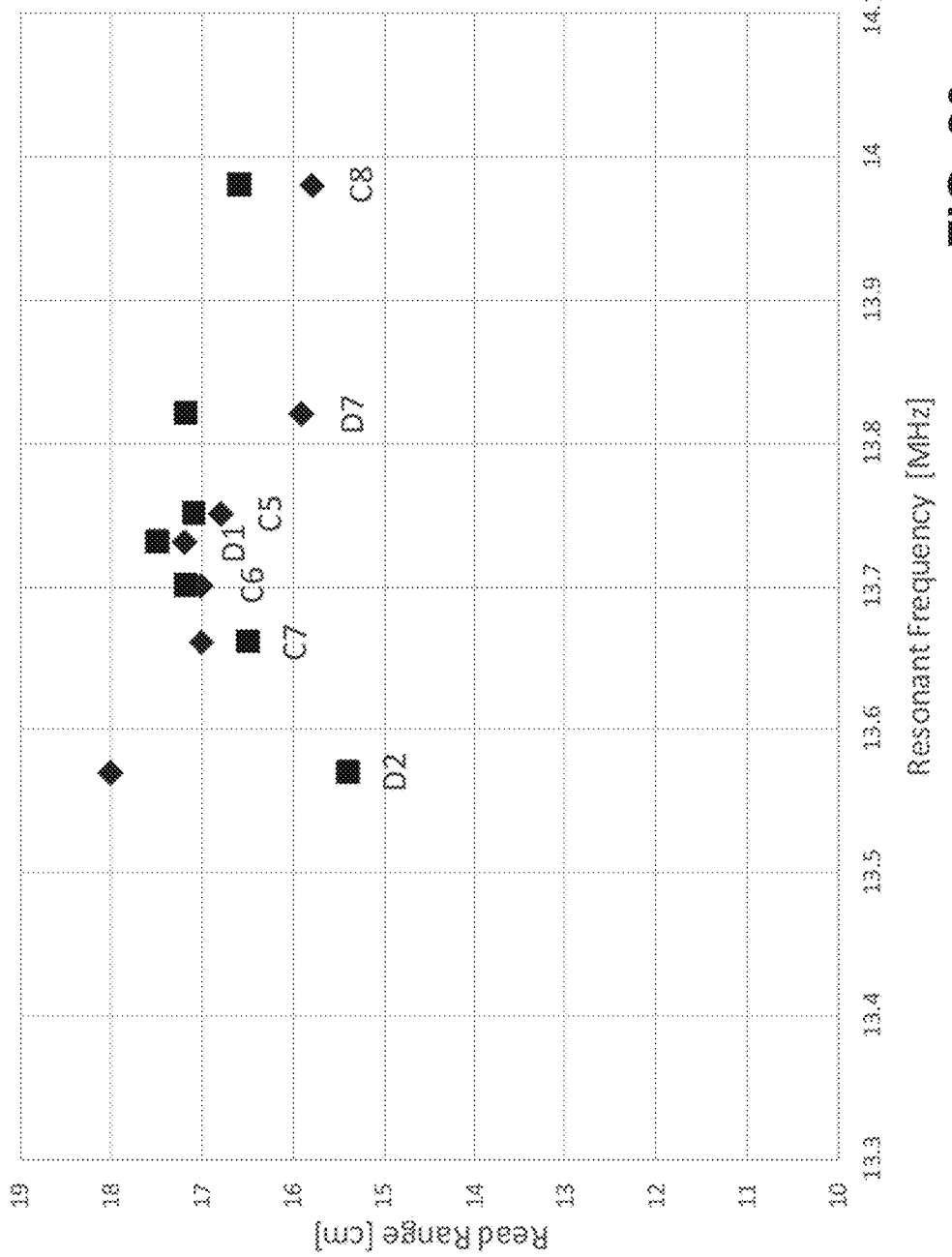
FIG. 20 is a chart of measured read ranges versus resonant frequency for 000 size capsules in air and in saline from example experiments.
Figure 21:
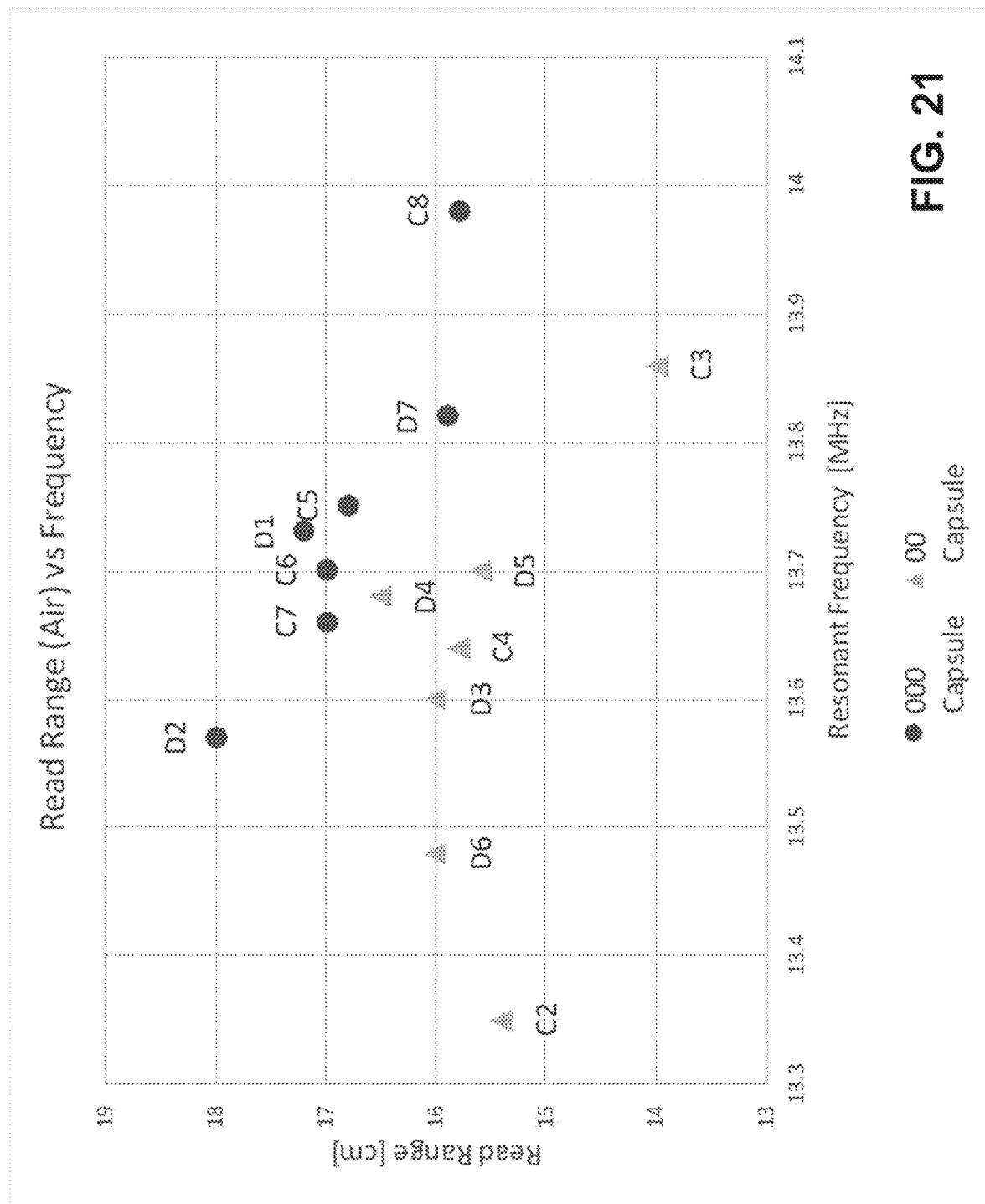
FIG. 21 is a chart of measured read ranges versus resonant frequency in air for various capsule types from example experiments.

Additional bench experiments were performed to determine the read range of various RFID tag configurations (having the general configuration of FIGS. 8A and 8B) placed in the tubular configuration into capsules utilizing different RFID reader configurations. The RFID tag and RFID reader information from the additional bench experiments is shown in the table of FIG. 18, with a 90 mm reader antenna being utilized for all measurements. A chart of the measured read ranges versus resonant frequency for the 00 size capsules in air and in saline is shown in FIG. 19, where identification of the individual capsules corresponds to the "SN" value from FIG. 18. A chart of the measured read ranges versus resonant frequency for the 000 size capsules in air and in saline is shown in FIG. 20, where identification of the individual capsules corresponds to the "SN" value from FIG. 18. A chart of the measured read ranges versus resonant frequency in air for all capsule types is shown in FIG. 21, where identification of the individual capsules corresponds to the "SN" value from FIG. 18. A chart of the measured read ranges versus resonant frequency in saline for all capsule types is shown in FIG. 22, where identification of the individual capsules corresponds to the "SN" value from FIG. 18.

One skilled in the art will recognize that the herein described component, devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components, devices, and objects should not be taken as limiting.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A radio frequency identification (RFID) system, comprising:
    an RFID tag including
    a flexible substrate foldable between a planar configuration and a tubular configuration,
    a conductive element disposed at least on a first side of the flexible substrate, and
    an RFID tag chip disposed at least on the first side of the flexible substrate electrically coupled with the conductive element;
    a capsule structured and dimensioned for ingestion by a biological subject, the capsule including a shell structured and dimensioned to enclose a medication for the biological subject simultaneously with the RFID tag when the flexible substrate is in the tubular configuration, but not when the flexible substrate is in the planar configuration;
    an RFID reader including a coil structured and dimensioned to interrogate the RFID tag within the biological subject; and
    a pH switch structure coupled to an exterior surface of the capsule, the pH switch configured to deactivate the RFID tag in a first configuration of the pH switch structure and to permit activation of the RFID tag in a second configuration of the pH switch structure within the biological subject, wherein the pH switch structure includes an electrically conductive material having a shorted turn structure coupled to the exterior surface of the capsule, the shorted turn structure configured to absorb energy transmitted between an RFID reader and the RFID tag.

2. The system of claim 1, wherein the first configuration of the pH switch structure includes a first structural integrity of the pH switch structure, and wherein the second configuration of the pH switch structure includes a second structural integrity of the pH switch structure different than the first structural integrity.

3. The system of claim 1, wherein the pH switch structure includes an electrically conductive material surrounding the capsule.

4. The system of claim 3, wherein the electrically conductive material is directly coupled to the exterior surface of the capsule.

5. The system of claim 3, wherein the electrically conductive material is coupled to the exterior surface of the capsule via an intervening acid-soluble substrate.

6. The system of claim 5, wherein the acid-soluble substrate is dissolvable in an acidic environment having a pH at or below 5.0 and is not substantially dissolvable at a pH above 6.0.

7. The system of claim 1, wherein the electrically conductive material is directly coupled to the exterior surface of the capsule.

8. The system of claim 1, wherein the electrically conductive material is coupled to the exterior surface of the capsule via an intervening acid-soluble substrate.

9. The system of claim 8, wherein the acid-soluble substrate is dissolvable in an acidic environment having a pH at or below 5.0 and is not substantially dissolvable at a pH above 6.0.

10. The system of claim 1, wherein the shorted turn structure includes a first electrically conductive material and a second electrically conductive material, wherein the second electrically conductive material has a thickness normal to the exterior surface of the capsule that is greater than the first electrically conductive material.

11. The system of claim 1, wherein the shorted turn structure includes a first portion having a first material thickness of the electrically conductive material normal to the exterior surface of the capsule and a second portion having a second material thickness of the electrically conductive material normal to the exterior surface of the capsule, wherein the second thickness is greater than the first thickness.

12. The system of claim 1, further including one or more tuning capacitors coupled to the flexible substrate.

13. The system of claim 1, wherein the conductive element includes a coil configuration including a plurality of turns disposed on the first side of the flexible substrate.

14. The system of claim 1, wherein the conductive element includes
    a first coil configuration including a plurality of turns disposed on the first side of the flexible substrate; and
    a second coil configuration including a plurality of turns disposed on an opposing side of the first side of the flexible substrate.

15. The system of claim 14, wherein the plurality of turns of the first coil configuration is the same as the plurality of turns of the second coil configuration.

16. A radio frequency identification (RFID) system, comprising: a capsule structured and dimensioned for ingestion by a biological subject, the capsule including a shell structured and dimensioned to enclose a medication for the biological subject simultaneously with the RFID tag;
    the RFID tag including
    a flexible substrate formed in a structure for positioning within the capsule,
    a conductive element disposed at least on a first side of the flexible substrate, and
    an RFID tag chip disposed at least on a second side of the flexible substrate;

an RFID reader including a coil structured and dimensioned to interrogate the RFID tag within the biological subject; and a pH switch structure coupled to an exterior surface of the capsule, the pH switch configured to deactivate the RFID tag in a first configuration of the pH switch structure and to permit activation of the RFID tag in a second configuration of the pH switch structure within the biological subject, wherein the pH switch structure includes an electrically conductive material having a shorted turn structure coupled to the exterior surface of the capsule, the shorted turn structure configured to absorb energy transmitted between the RFID reader and the RFID tag.

17. The system of claim 16, wherein the first configuration of the pH switch structure includes a first structural integrity of the pH switch structure, and wherein the second configuration of the pH switch structure includes a second structural integrity of the pH switch structure different than the first structural integrity.

18. The system of claim 16, wherein the pH switch structure includes an electrically conductive material surrounding the capsule.

19. The system of claim 18, wherein the electrically conductive material is directly coupled to the exterior surface of the capsule.

20. The system of claim 18, wherein the electrically conductive material is coupled to the exterior surface of the capsule via an intervening acid-soluble substrate.

21. The system of claim 16, wherein the electrically conductive material is directly coupled to the exterior surface of the capsule.

22. The system of claim 16, wherein the electrically conductive material is coupled to the exterior surface of the capsule via an intervening acid-soluble substrate.

23. The system of claim 16, wherein the shorted turn structure includes a first electrically conductive material and a second electrically conductive material, wherein the second electrically conductive material has a thickness normal to the exterior surface of the capsule that is greater than the first electrically conductive material.

24. The system of claim 16, wherein the shorted turn structure includes a first portion having a first material thickness of the electrically conductive material normal to the exterior surface of the capsule and a second portion having a second material thickness of the electrically conductive material normal to the exterior surface of the capsule, wherein the second thickness is greater than the first thickness.

25. The system of claim 16, wherein the capsule includes an end cap structured and dimensioned to enclose the RFID tag chip.

* * * * *